United States Patent
De Kort et al.

(10) Patent No.: US 8,183,228 B2
(45) Date of Patent: *May 22, 2012

(54) ANTICOAGULANT ANTITHROMBOTIC DUAL INHIBITORS COMPRISING A BIOTIN LABEL

(75) Inventors: Martin De Kort, Oss (NL); Constant Adriaan Anton Van Boeckel, Oss (NL); Charles David Nicholson, Oss (NL)

(73) Assignee: MSD OSS B.V. Netherlands, Rahway, NJ (US)

( * ) Notice: Subject to any disclaimer, the term of this patent is extended or adjusted under 35 U.S.C. 154(b) by 457 days.

This patent is subject to a terminal disclaimer.

(21) Appl. No.: 12/083,212

(22) PCT Filed: Oct. 6, 2006

(86) PCT No.: PCT/EP2006/067127
§ 371 (c)(1),
(2), (4) Date: Apr. 16, 2009

(87) PCT Pub. No.: WO2007/042469
PCT Pub. Date: Apr. 19, 2007

(65) Prior Publication Data
US 2010/0029582 A1    Feb. 4, 2010

(30) Foreign Application Priority Data

Oct. 10, 2005  (EP) .................... 05109403
Oct. 25, 2005  (EP) .................... 05109962

(51) Int. Cl.
*A61K 31/715*  (2006.01)
*C07H 3/06*    (2006.01)

(52) U.S. Cl. ..................... 514/54; 536/123.1

(58) Field of Classification Search .......... 514/54; 536/123.1
See application file for complete search history.

(56) References Cited

U.S. PATENT DOCUMENTS 6,486,129 B1 * 11/2002 Tromp et al. ............ 514/32
7,576,071 B2 * 8/2009 Buijsman et al. ........ 514/54

FOREIGN PATENT DOCUMENTS

EP  1574516 A1 * 9/2005
WO WO 02/024754 A1 * 3/2002

* cited by examiner

*Primary Examiner* — Shaojia Anna Jiang
*Assistant Examiner* — Ganapathy Krishnan
(74) *Attorney, Agent, or Firm* — Richard S. Parr; Catherine D. Fitch

(57) ABSTRACT

The present invention relates compounds of the formula: oligosaccharide-spacer-(GpIIb/IIIa antagonist), wherein the oligosaccharide is a negatively charged oligosaccharide residue comprising four to twenty five monosaccharide units, the charge being compensated by positively charged counterions, and wherein the oligosaccharide residue is derived from an oligosaccharide which has (AT-III mediated) anti-Xa activity per se; the spacer is a bond or an essentially pharmacologically inactive linking residue; the GpIIb/IIIa antagonist is a residue mimicking the RGD and/or K(QA)GD fragment of fibrinogen, comprising a carboxylate moiety and a basic moiety located within the residue at a distance of 10-20 Å from each other; or a pharmaceutically acceptable salt thereof or a prodrug or a solvate thereof; wherein the compound of formula I further comprises at least one covalent bond with a biotin label or an analogue thereof. The compounds of the invention have antithrombotic activity and can be used in treating or preventing thrombotic diseases. The antithrombotic activity of the compound of this invention can be neutralized in case of emergency upon administration of avidin, streptavidin and analogues thereof having high biotin affinity.

7 Claims, 5 Drawing Sheets

ANTICOAGULANT ANTITHROMBOTIC DUAL INHIBITORS COMPRISING A BIOTIN LABEL

CROSS REFERENCE TO RELATED APPLICATION

Figure 1:
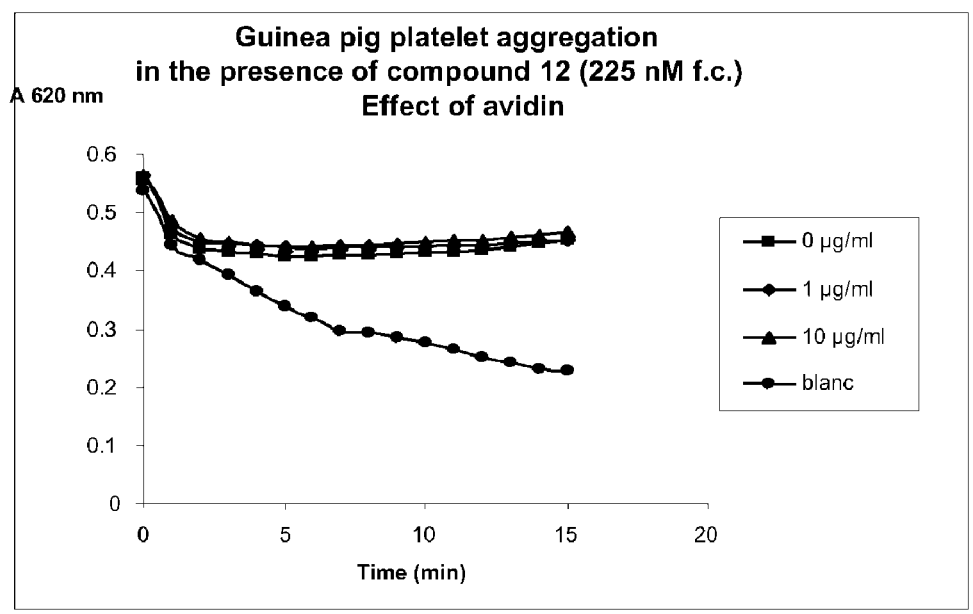

This application claims priority based on International Patent Application No. PCT/EP2006/067127, filed on Oct. 6, 2006.

FIELD OF THE INVENTION

The present invention relates to new antithrombotic dual inhibitors comprising a biotin label or a biotin derivative, a process for their preparation, pharmaceutical compositions containing the compounds as active ingredients, as well as the use of said compounds for the manufacture of medicaments.

BACKGROUND OF THE INVENTION

Recent progress in the search for GPIIb/IIIa antagonists having a predictable antithrombotic effect, preferably with a longer half-life (to achieve consistent levels of inhibition of platelet aggregation), has resulted in new antithrombotic dual inhibitors which have a mixed pharmacological profile. These new compounds inhibit two key targets in both the coagulation cascade (factor Xa) and the platelet aggregation pathway (GpIIb/IIIa) (described in EP 1574516).

As a precautionary measure, within the field of anticoagulant and anti-atherothrombotic therapy, there is a need for an antidote to be able to effectively neutralize or minimize the activity of the anticoagulant or anti-atherothrombotic drug used. This is because it is well known that a hemorrhage can be triggered in a patient under treatment for any accidental cause. Further, it may be necessary to intervene surgically in a patient under anti-atherothrombotic or anticoagulant treatment. In addition, during some surgical procedures, anticoagulants may be used at a high dose so as to prevent blood coagulation and it is necessary to neutralize them at the end of the operation. Further, clinically effective antidotes are not yet available in anti-platelet therapy wherein GpIIb/IIIa inhibitors are used. It is therefore advantageous to have anti-atherothrombotic and/or anticoagulant agents available which can be neutralized in order to stop the anti-atherothrombotic and/or anticoagulant activity at any time.

In US 2004/0024197 (WO02/24754) it is disclosed that, in case of emergency, the anticoagulant activity of certain polysaccharides may be partially reduced using avidin, if those polysaccharides contain at least a covalent bond with biotin or a biotin derivative.

O. Roger et al. in Carbohydrate Polymers 50 (2002) 273-278 discuss carbohydrate derivatisation by reductive amination, including biotinylation agents. The disclosure relates to the aselective modification of polydisperse natural polysaccharides.

DETAILED DESCRIPTION OF THE INVENTION

The present invention relates to novel neutralizable dual inhibitors derived from the dual inhibitors described in EP 1574516. It has been found that a certain biotin "label", being the group

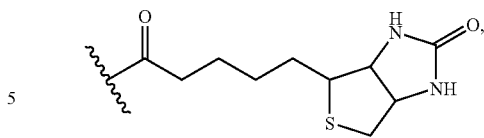

also referred to in this document as "BT" (derived from hexahydro-2-oxo-1H-thieno[3,4-d]imidazole-4-pentanoic acid, preferably the D(+)-isomer) or an analogue thereof, can be attached to or introduced into the structure of the compounds described in EP 1574516, resulting in neutralizable dual inhibitors.

Thus, the present invention relates to compounds of the formula (I)

$$\text{oligosaccharide-spacer-GpIIb/IIIa antagonist} \qquad (I),$$

wherein
the oligosaccharide is a negatively charged oligosaccharide residue comprising four to twenty five monosaccharide units, the charge being compensated by positively charged counterions, and wherein the oligosaccharide residue is derived from an oligosaccharide which has (AT-III mediated) anti-Xa activity per se;
the spacer is a bond or an essentially pharmacologically inactive linking residue;
the GpIIb/IIIa antagonist is a residue mimicking the RGD and/or K(QA)GD fragment of fibrinogen, comprising a carboxylate moiety and a basic moiety located within the residue at a distance of 10-20 Å from each other;
or a pharmaceutically acceptable salt thereof or a prodrug or a solvate thereof; wherein the compound of formula I further comprises at least one covalent bond with a biotin label or an analogue thereof.

The compounds of the invention are effective antithrombotic agents by both ATIII-mediated inhibition of coagulation factor Xa and inhibition of platelet aggregation by antagonizing the binding of fibrinogen to its receptor. They are useful for treating and (possibly) for preventing thrombotic diseases. This includes a number of thrombotic and prothrombotic states in which the coagulation cascade is activated, which include—but are not limited to—deep vein thrombosis, pulmonary embolism, thrombophlebitis, arterial occlusion from thrombosis or embolism, arterial reocclusion during or after angioplasty, restenosis following arterial injury or invasive cardiological procedures, postoperative venous thrombosis or embolism, stroke and myocardial infarction.

The biotin label (or analogue thereof) in the compounds of the present invention is rapidly recognized by and binds to a specific antidote, being avidin (The Merck Index, Twelfth edition, 1996, M.N. 920, pages 151-152) or streptavidin, two tetrameric proteins with respective masses equal to approximately 66 000 and 60 000 Da which have a very high affinity for biotin. Thus, in an emergency situation, the action of the dual inhibitor of this invention can be rapidly neutralized by using avidin or streptavadin, for example by injection of a pharmaceutical solution containing the same. Analogues of avidin and streptavidin having high biotin affinity may be used similarly. The resulting inactive antidote-inhibitor complex is cleared from the blood circulation.

It has been found in comparative studies with the corresponding non-biotinylated compounds that the introduction of a biotin label into the dual inhibitors does not interfere with their platelet aggregation inhibitory activity nor with their anti-thrombin III (AT-III) mediated anti-Xa potency. In addition, administration of avidin or streptavidin leads to fast and up to quantitative neutralization of the antithrombotic activity of the compounds of formula I.

Biotin analogues, which may be used as a label according to this invention, may be selected from, but are not limited to, the biotin analogues shown in the Pierce catalogue, 1999-2000, pages 62 to 81, for example 6-biotinamidohexanoate, 6-(6-biotinamidohexanamido)hexanoate, and 2-biotinamidoethanethiol, etc. In such analogues the biotin label BT, as previously defined, is a characteristic part of the structure. Other analogues are for example biotin analogues that are alkyated at the biotinamide bond (wherein alkyl is (1-4C)alkyl, preferably methyl), which are stable to biotinidase cleavage, or other biotin analogues comprising for example a hydroxymethylene, carboxylate, or acetate alpha to the biotinamide bond.

Preferred biotin analogues have the formula —(NH—CO)$_n$—(CH$_2$)$_p$—X-BT, wherein n is 0 or 1, p is 4 or 5, X=NH, N(1-4C)alkyl, —NH—CH(CH$_2$OH)—CH$_2$—C(O)—NH—, —NH—CH(CH$_3$)—CH$_2$—C(O)—NH—, —NH—CH(COOH)—CH$_2$—C(O)—NH—, —NH—CH(CH$_2$COOH)—CH$_2$—C(O)—NH—, and BT is as previously defined.

Any negatively charged oligosaccharide residue of four to twenty five monosaccharide units is usable in the compounds of the present invention. Suitable compounds of the invention are compounds wherein the oligosaccharide is a sulfated oligosaccharide residue. Preferably, the oligosaccharide residue is derived from an oligosaccharide which has (AT-III mediated) anti-Xa activity per se, such as the oligosaccharides disclosed in EP 0,454,220, EP 0,529,715, WO 97/47659, WO 98/03554 and WO 99/36443. Further preferred are oligosaccharide residues having four to sixteen monosaccharide units. Most preferably the oligosaccharide is a sulfated pentasaccharide residue. Preferred pentasaccharide residues have the structure A

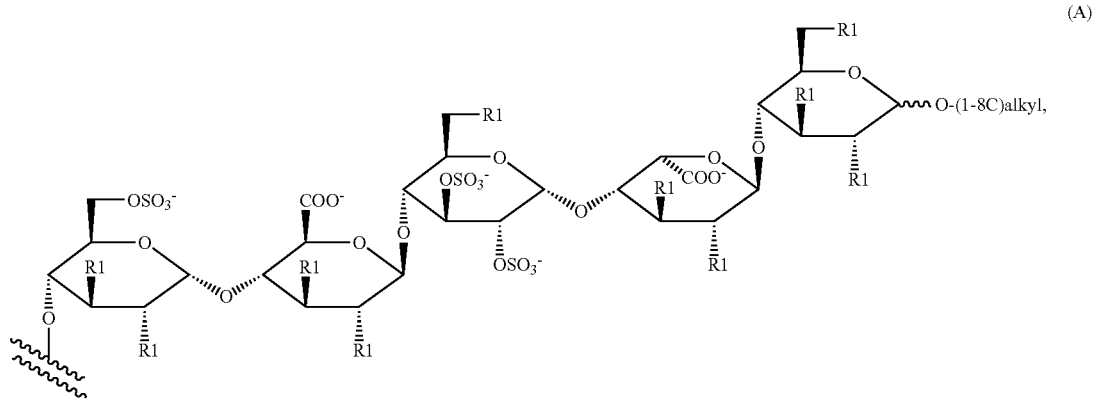

wherein R1 is independently a biotin label or analogue thereof, OSO$_3^-$ or (1-8C)alkoxy. Particularly preferred pentasaccharides have the structure B

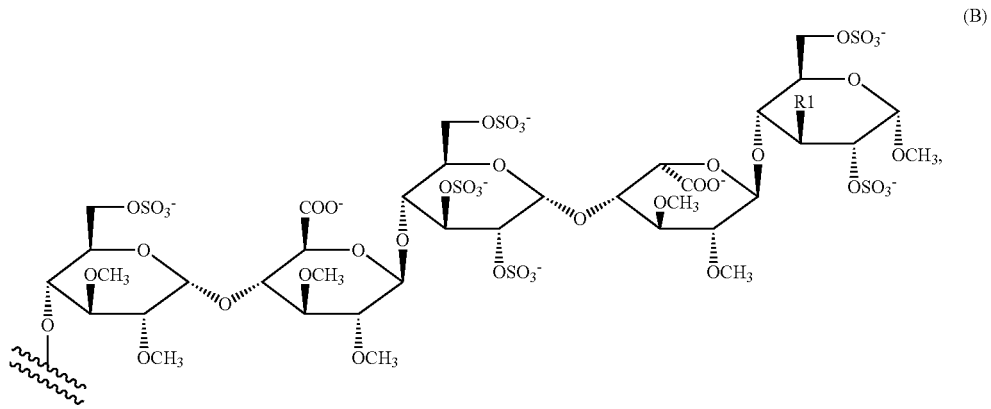

wherein R1 is OCH$_3$ or OSO$_3^-$. In the most preferred pentasaccharide of the structure B R1 is OSO$_3^-$.

The spacer is a bond or an essentially pharmacologically inactive, flexible, linking residue. The term "essentially pharmacologically inactive" as used herein means that the spacer does not contain atoms or groups which show pharmacologically activity per se at the doses at which the compounds of the invention are therapeutically effective. Thus, at doses at which the compounds of the present invention are used as antithrombotics, the nature of the spacer does not lead to demonstrable pharmacological side-effects. In preferred embodiments the spacer is an essentially pharmacologically inactive linking residue, preferably having 1-50 atoms counted along the "backbone" of the spacer, the oxygen of the oligosaccharide residue not included. The spacer may comprise (somewhat) rigid elements, such as ring structures and unsaturated bonds. The spacer of the compounds of the invention is preferably flexible. Suitable spacers may easily be designed by a person skilled in the art. A more preferred length of the spacer is 10-35 atoms, in particular 10-28. For synthetic reasons longer spacers are considered less suitable, however, longer spacers may still successfully be applied in the compounds of the present invention. Highly suitable spacers comprise at least one —(CH$_2$CH$_2$O)— element. More preferred spacers comprise more, preferably six —(CH$_2$CH$_2$O)— elements.

The attachment site of the spacer to the GpIb/IIIa antagonist residue may be chosen essentially arbitrarily, provided that the GpIIb/IIIa antagonist activity is not abolished. Thus, the typically present carboxylate moiety (optionally esterified) and basic moiety must remain unaffected.

In preferred compounds according to this invention, the GpIIb/IIIa antagonist residue is selected from residues derived from Ro 435054, SC 54701 (xemilofiban), RWJ 50042, sibrafiban (Ro 44 3888), lamifiban (Ro 449883), GPI 562, FK 633, tirofiban (MK 383), orbofiban (SC 57101), eptifibatide (C68 22), roxifiban (XV 459), elarofiban (RWJ 53308), SR 121787, lefradafiban (BIBU 52), lotrafiban (SB 214857), gantofiban (YM 028), T-250, EF 5077, ZD 2486, TAK 029, TP 9201, L 703014, SR 121566 (active form of SR 121787) and UR-3216. Derivatives of said residues also include chemically modified residues, wherein the part comprising the (optionally esterified) carboxylate moiety and a basic moiety (or protected basic moiety) is retained. In a preferred embodiment, SR 121566 (active form of SR 121787) is selected. Most preferred are compounds wherein GpIIb/IIIa antagonist residue is derived from tirofiban.

Preferred compounds according to the invention comprise one covalent bond with a biotin label or analogue thereof.

The biotin (or analogue thereof) label may be present in all parts of the compound formula I. Therefore, embodiments of this invention are compounds wherein (a) the oligosaccharide residue of the compound of formula I comprises a covalent bond with a biotin label or analogue thereof, (b) the spacer of the compound of formula I comprises a covalent bond with a biotin label or analogue thereof and (c) the GpIIb/IIIa antagonist residue of the compound of formula I comprises a covalent bond with a biotin label or analogue thereof.

Preferred are compounds comprising one covalent bond with a biotin analogue, wherein the oligosaccharide residue of the compound of formula I comprises one covalent bond with a biotin analogue of the formula —(NH—CO)$_n$—(CH$_2$)$_p$—X-BT, wherein n is 0 or 1 (in these compounds preferably n=1), p is 4 or 5 (in these compounds preferably p=5), X and BT are as previously defined.

Other preferred compounds of the invention comprise one covalent bond with a biotin analogue, wherein the spacer of the compound of formula I comprises one covalent bond with a biotin analogue of the formula —(CH$_2$)$_4$—X-BT, wherein X and BT are as defined previously.

Representative examples of the biotinylated dual inhibitors of the present invention have the structures

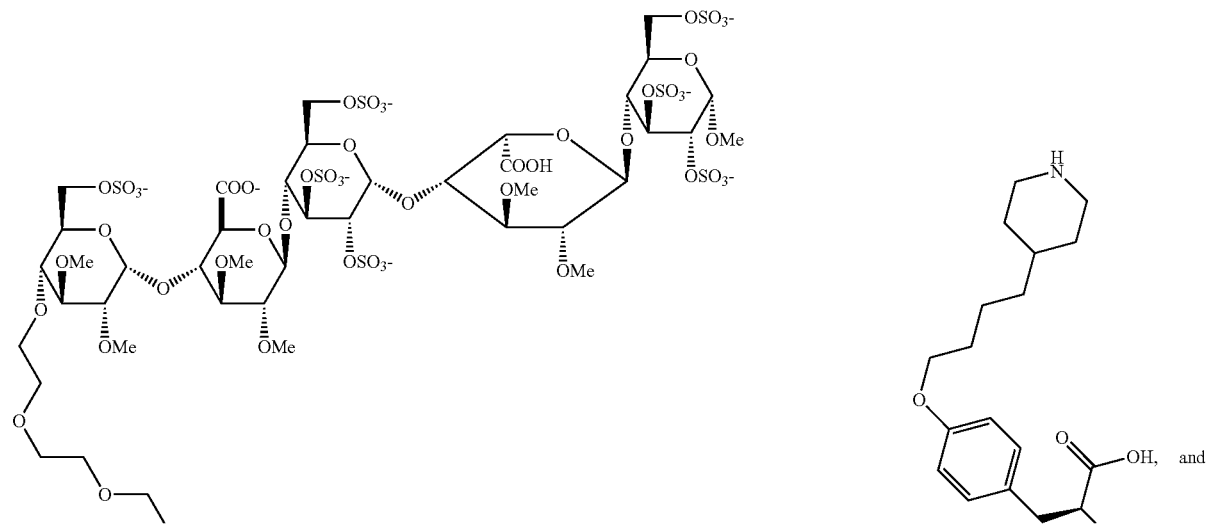

(II)

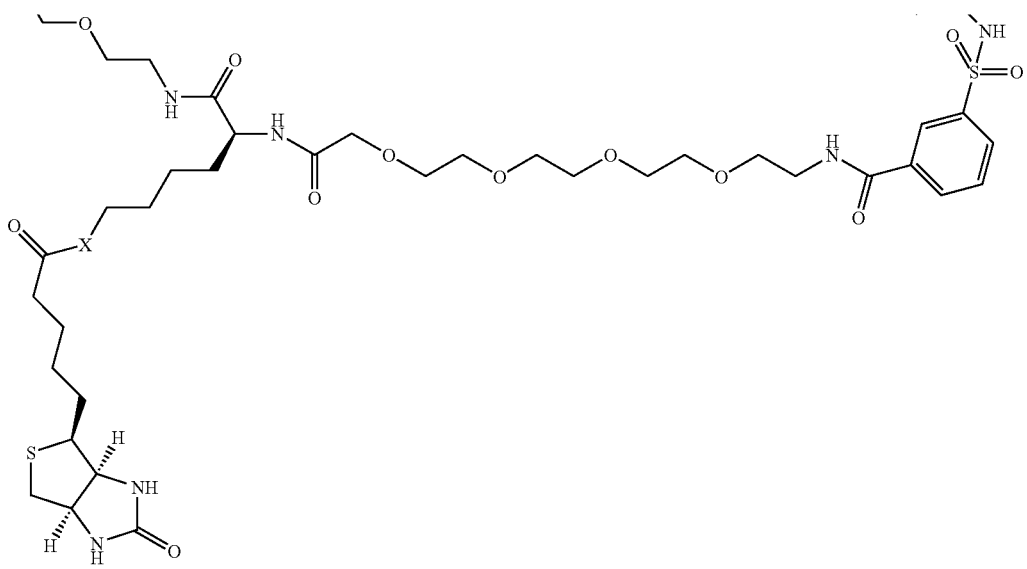
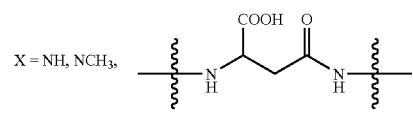
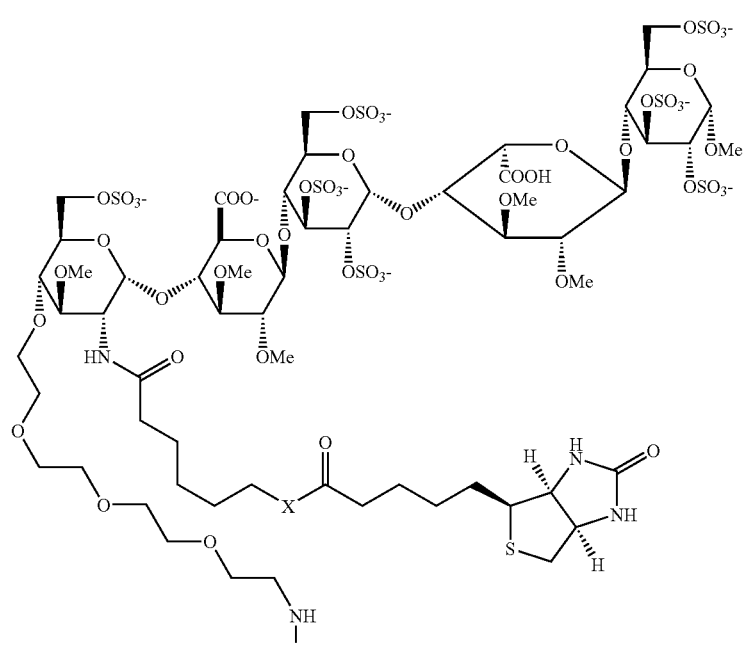
(III)

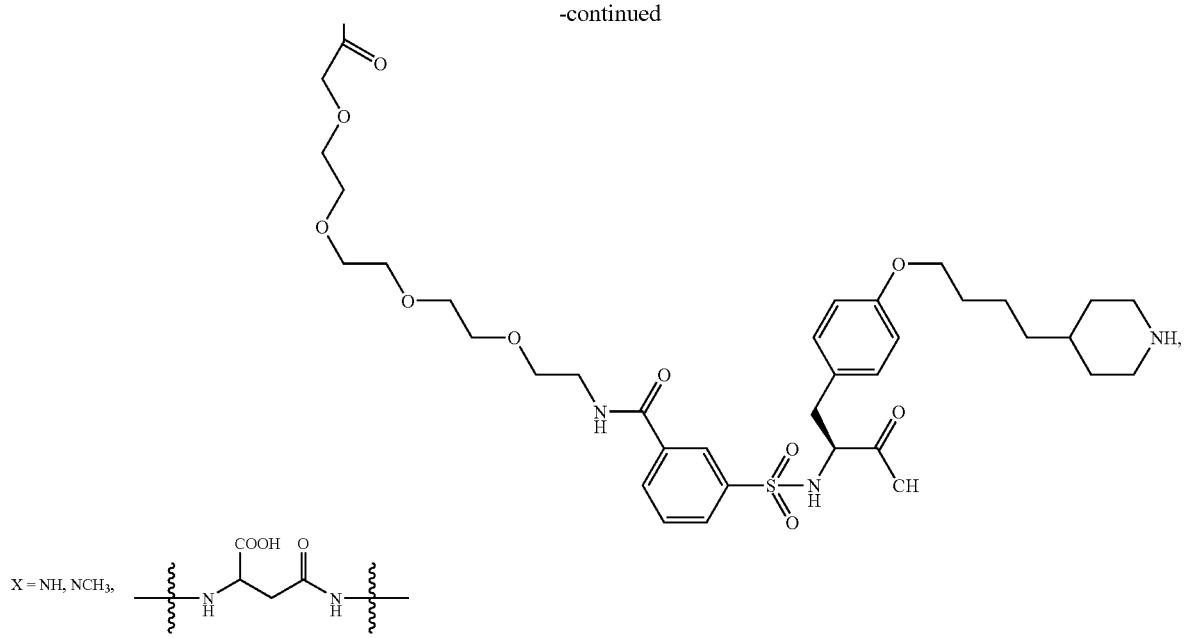

but also compounds of formula I, wherein the spacer is attached to the oligosaccharide at another position, and/or compounds wherein the biotin (analogue) label is present at other positions of the molecule. The compounds of formula II are preferred examples of this invention.

A positively charged counterion means $H^+$, $Na^+$, $K^+$, $Ca^{2+}$, and the like. Preferably the compounds of formula I are in the form of their sodium salt.

The term basic moiety means any well known basic moiety, such as an amine, amidine guanidine, piperidine, and the like.

With the phrase "at a distance of 10-20 Å from each other" the spatial orientation of the two groups with respect to another is meant, not only measured along the bonds. Well known modelling techniques are available to the person skilled in the art for the determination of the distance. (See for example J. Med. Chem. 1994, 37, 2537-2551).

The term (1-8C)alkyl means a branched or unbranched alkyl group having 1-8 carbon atoms, for example methyl, ethyl, propyl, isopropyl, butyl, sec-butyl, tert-butyl, hexyl and octyl. Methyl and ethyl are preferred alkyl groups.

In the term (1-8C)alkoxy, the alkyl residue is as defined previously.

The term "prodrug" means a compound which is metabolized in the body into the active compound, e.g. a compound in which the basic moiety (such as an amino or benzamidino group) in the GpIIb/IIIa antagonist residue of the compound of formula I is protected, e.g. by a hydroxy, (1-6C)alkoxy or (1-6C)alkoxycarbonyl group. Also examples of prodrugs are compounds of formula I, wherein the carboxylate group in the GpIIb/IIIa antagonist residue is esterified.

Solvates according to the invention include hydrates.

The compounds of the present invention can be prepared by optionally modifying earlier described GPIIb/IIIa antagonists which are e.g. derived from tirofiban, SR 121566, Ro 435054, RWJ 50042 or SC 54701 (the pharmacologically active form of xemilofiban), lamifiban, or analogues thereof, with amino acids, peptidomimetics or additional functional groups (e.g. —COOH, —$NH_2$, —SH, —OH, —$N_3$, terminal alkyne or the like) using methods generally known in the art. An example of the synthesis of such a modified RGD-analog is described in Bioorganic Chemistry 29, 357-379 (2001), where the compound is suggested as a potential vector for targeted drug delivery. According to the invention, the optionally modified GPIIb/IIIa antagonist part (a) is coupled directly to an oligosaccharide or (b) is coupled to an oligosaccharide-spacer residue or (c) is coupled to a spacer, which is subsequently coupled to an oligosaccharide-spacer-residue (e.g. by methods known from WO 99/65934; WO 01/42262). Any suitable oligosaccharide may be used for this purpose, for example oligosaccharides known in literature (e.g. from EP 0,454,220 and EP 0,529,715, but not limited to these sources) or commercially available oligosaccharides. The oligosaccharides may be phosphorylated at an appropriate point in time by methods known in the art, e.g. as described by Buijsman, R. et al. (*Bioorg. Med. Chem. Lett.* 1999, 9, 2013-2018). The coupling of the spacer to the oligosaccharide can for instance be performed by using the methods described in EP 0,649,854 or EP 04005343.1.

With regard to the way in which the biotin label is attached to compounds of the formula I the chemical literature offers several possibilities which can be utilized and by which different sets of protective groups well known to a person skilled in the art can be employed. The biotin label, comprising a reactive group of for instance the activated ester, maleimide, iodoacetyl or primary amine type, will preferably be reacted with an amine functional group, or a thiol functional group, or a carboxylic acid functional group, or an aldehyde functional group, the reaction taking place according to the conditions described in the literature (cf. Savage et al., Avidin-Biotin Chemistry: A Handbook; Pierce Chemical Company, 1992).

The biotin label can for instance be bonded directly to the (negatively charged) oligosaccharide residue or via an optionally N-(1-4C)alkylated amino functional group of a oligosaccharide-spacer residue or via an optionally N-(1-4C) alkylated amino acid residue to an optionally N-(1-4C)alkylated amine functional group of the oligosaccharide residue of the compound of formula I.

In another aspect of this invention the biotin label can for instance be bonded directly to the GpIIb/IIIa antagonist residue or via an optionally N-(1-4C)alkylated amino functional group of a linking residue or via an optionally N-(1-4C) alkylated amino acid residue to an optionally N-(1-4C)alkylated amine functional group of the GpIIb/IIIa antagonist residue of the compound of formula I.

Yet in another aspect of this invention the biotin label can for instance be introduced stepwise by first bonding directly to the GpIIb/IIIa antagonist residue or via an optionally N-(1-4C)alkylated amino functional group of a part of the spacer of formula I or via an optionally N-(1-4C)alkylated amino acid residue to an optionally N-(1-4C)alkylated amine functional group of the GpIIb/IIIa antagonist residue of the compound of formula I and second bonding directly to an oligosaccharide or via an optionally N-(1-4C)alkylated amino functional group of part of the spacer of formula I or via an optionally N-(1-4C)alkylated amino acid residue to an optionally N-(1-4C)alkylated amine functional group of the (negatively charged) oligosaccharide of the compound of formula I, or vice versa.

In another aspect of the invention optionally N-alkylated amino acid residues or α-N-substituted (beta-)amino acid analogues may be introduced by a peptide coupling using methods known in the art. The azido group is a suitable latent amine functional group which can be used in precursors of the compound of the formula I for the subsequent introduction of the biotin label.

Also other examples of known GpIIb/IIIa antagonists may serve as the (basis for the) GpIIb/IIIa antagonist part of the compounds of the present invention (but not limited to these examples): the compounds Ro 43 8857, Ro 48 3657, BIBL 12, FK 633, GR 144053, EMD 76 334, SR 121566, SB 208651, SC 54684, SC 52012, DMP 754, FR 158999, GR 200976, XV 788, MK 383 (tirofiban), RWJ 53308, ZD 2486, L 709780, RGD 891, T 250, C 6822, BIBU 104, SB 214857, SC 57101, G 7453, TAK 029, XV 454, XV 459, L 734 217, DMP 802, SR 121787, TP 9201, DMP 757, SC 52012, RPR 109891, YM 68128, ME 3229, ME 3230, CT 50352, MK 852, S 1197, DMP 728, SC 57345, L 738 167, GR 233548, Ro 438857, TA 993, YM 337, BIBW 194, BIBU 129, BIBW 98, tetrafibricin, L 703 014, BIBU 251, GR 91669, RG 13965, G 7446, PS 028, XR 300, NSL 9403, L 756568, S 1762, L 746 223, L 767685, NSL 95301, G 4120, SB 207043, GR 83895, P246, L 739 758, XR 299, SV 873, RWJ 50228, XQ 870, EF 5154, AR 0510, G 7570, G 7442, G 7464, RWJ 52656, TAK 024, MS 180, MS 28168, XU 063, XU 065, L 734115, SM 20302, TS 943, NSL 96184, UR 12947, XU 057, L 750034, UR 3216, UR 2922, CP 4632, AR 0598, SC 79992, SC 4992, RGD 039, ME 3277, T 250, SC 57099B, SKF 106760, SKF 107260, RWJ 52654, PSA 0613, CGH 400, NSL 95317, XT 111, RWJ 27755, L 736622, SC 46749, SM 20302, YM 570029, CY 311176 and GpIIb/IIIa antagonists described in EP 0,529,858, WO 96/20172, EP 0,496,378, EP 0,530,505, Bioorg. & Med. Chem. 3, 539 (1995), WO 93/08174, J. Am. Chem. Soc. 115, 8861 (1993), J. Med. Chem. 43, 3453 (2000), Bioorg. Med. Chem. 3, 337 (1995), U.S. Pat. No. 5,239,113, U.S. Pat. No. 5,344,957, U.S. Pat. No. 5,973,003, U.S. Pat. No. 5,703,125, WO 96/37464, WO 93/07867, U.S. Pat. No. 5,378,712, EP 445,796, U.S. Pat. No. 5,273,982, U.S. Pat. No. 5,770,575, WO 01/602813, EP 656,348, U.S. Pat. No. 5,726,185, EP 505,868, EP 560,730, U.S. Pat. No. 5,561,112, EP 513,675, U.S. Pat. No. 5,574,016, WO 94/09030, EP 478,363, U.S. Pat. No. 5,292,756, U.S. Pat. No. 5,206,373, WO 93/16994, U.S. Pat. No. 5,312,923, EP 743, 302, U.S. Pat. No. 5,658,929, U.S. Pat. No. 5,880,136, U.S. Pat. No. 5,814,643, U.S. Pat. No. 6,040,317, Expert Opin. Ther. Patents 13 (8), 1173-1188 (2003) and Curr. Pharm. Design 14, 1567-1609 (2004).

Further included into the present invention are compounds comprising newly designed GpIIb/IIIa antagonist residues mimicking the RGD and/or K(QA)GD fragment of fibrinogen, typically comprising a carboxylate moiety (optionally esterified) and a basic moiety located within the residue at a distance of 10-20 Å from each other.

The peptide coupling, a procedural step in the above described method to prepare the compounds of the invention, can be carried out by methods commonly known in the art for the coupling—or condensation—of peptide fragments such as by the azide method, mixed anhydride method, activated ester method, the carbodiimide method, or, preferably, under the influence of ammonium/uronium salts like TBTU, especially with the addition of catalytic and racemisation suppressing compounds like N-hydroxysuccinimide, N-hydroxybenzotriazole and 7-aza-N-hydroxybenzotriazole. Overviews are given in *The Peptides, Analysis, Synthesis, Biology*, Vol 3, E. Gross and J. Meienhofer, eds. (Academic Press, New York, 1981) and *Peptides: Chemistry and Biology*, N. Sewald and H.-D. Jakubke (Wiley-VCH, Weinheim, 2002).

Amine functions present in the compounds may be protected during the synthetic procedure by an N-protecting group, which means a group commonly used in peptide chemistry for the protection of an α-amino group, like the tert-butyloxycarbonyl (Boc) group, the benzyloxycarbonyl (Z) group, the 9-fluorenylmethyloxycarbonyl (Fmoc) group or the phthaloyl (Phth) group, or may be introduced by demasking of an azide moiety. Overviews of amino protecting groups and methods for their removal is given in the above mentioned *The Peptides, Analysis, Synthesis, Biology*, Vol 3 and *Peptides: Chemistry and Biology*.

Amidine functions, if present, can be left unprotected in the coupling step, or can be protected using carbamate such as allyloxycarbonyl or benzyloxycarbonyl. The amidine function is preferably introduced under mild conditions by using the 1,2,4-oxadiazolin-5-one moiety as the precursor.

Carboxylic acid groups may be protected by a group commonly used in peptide chemistry for the protection of an α-carboxylic acid group, such as a tert-butyl ester. Carboxylic acid groups of modified GPIIb/IIIa antagonists are preferably protected as a benzyl ester. Removal of the protecting groups can take place in different ways, depending on the nature of those protecting groups. Usually deprotection takes place under acidic conditions and in the presence of scavengers or reductive conditions such as catalytic hydrogenation.

A prerequisite for conjugation of the GPIIb/IIIa antagonist to an oligosaccharide is the presence of an orthogonally reactive anchoring group, such as a carboxylate group, which can be coupled directly to an oligosaccharide residue or to an oligosaccharide-spacer derivative or via a spacer to an oligosaccharide-spacer derivative. To allow such conjugation in most cases additional modification of the GPIIb/IIIa antagonist is necessary.

Construction of the spacer-derived building blocks for the synthesis of compounds of the formula I can be achieved in various ways using methods known in the art, either in a linear fashion by the step-wise introduction of amino acids, their derivatives or peptidomimetics, or in convergent manner by block-coupling of intermediate constructs.

The compounds of the invention, which can occur in the form of a free base, may be isolated from the reaction mixture in the form of a pharmaceutically acceptable salt. The pharmaceutically acceptable salts may also be obtained by treating the free base of formula (I) with an organic or inorganic acid such as hydrogen chloride, hydrogen bromide, hydrogen iodide, sulfuric acid, phosphoric acid, acetic acid, propionic acid, glycolic acid, maleic acid, malonic acid, methanesulphonic acid, fumaric acid, succinic acid, tartaric acid, citric acid, benzoic acid, ascorbic acid and the like.

The compounds of this invention or intermediates thereof may possess chiral carbon atoms, and may therefore be obtained as a pure enantiomer, or as a mixture of enantiomers, or as a mixture containing diastereomers. Methods for obtaining the pure enantiomers are well known in the art, e.g. crystallization of salts which are obtained from optically active acids and the racemic mixture, or chromatography using chiral columns. For diastereomers straight phase or reversed phase columns may be used.

The compounds of the invention may be administered enterally or parenterally. The exact dose and regimen of these compounds and compositions thereof will necessarily be dependent upon the needs of the individual subject to whom the medicament is being administered, the degree of affliction or need and the judgement of the medical practitioner. In general parenteral administration requires lower dosages than other methods of administration which are more dependent upon absorption. However, the daily dosages are for humans preferably 0.0001-10 mg per kg body weight, more preferably 0.001-1 mg per kg body weight.

The medicament manufactured with the compounds of this invention may also be used as adjuvant in (acute) antithrombotic therapy. In such a case, the medicament is administered with other compounds useful in treating such disease states, such as aspirin, clopidogrel or statins. Mixed with pharmaceutically suitable auxiliaries, e.g. as described in the standard reference, Gennaro et al., Remington's Pharmaceutical Sciences, (18th ed., Mack Publishing Company, 1990, see especially Part 8: Pharmaceutical Preparations and Their Manufacture) the compounds may be compressed into solid dosage units, such as pills, tablets, or be processed into capsules or suppositories. By means of pharmaceutically suitable liquids the compounds can also be applied in the form of a solution, suspension, emulsion, e.g. for use as an injection preparation.

For making dosage units, e.g. tablets, the use of conventional additives such as fillers, colorants, polymeric binders and the like is contemplated. In general any pharmaceutically acceptable additive which does not interfere with the function of the active compounds can be used. Suitable carriers with which the compositions can be administered include lactose, starch, cellulose derivatives and the like, or mixtures thereof, used in suitable amounts.

LEGENDS TO THE FIGURES

FIG. 1: Effect of avidin on the inhibition of the platelet aggregation by compound 12. Pre-incubation of compound and avidin.

Figure 2:
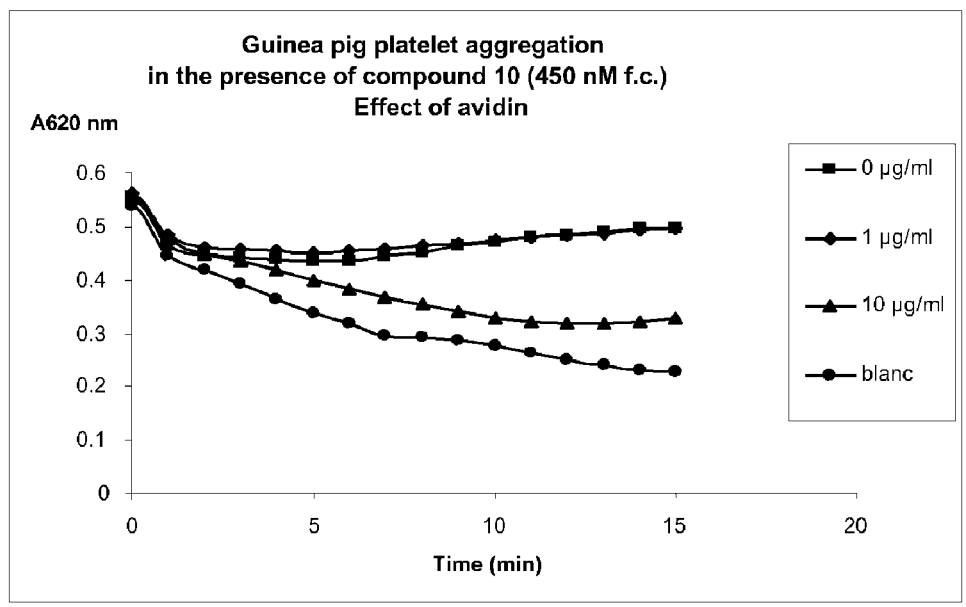

FIG. 2: Effect of avidin on the inhibition of the platelet aggregation by compound 10. Pre-incubation of compound and avidin.

Figure 3:
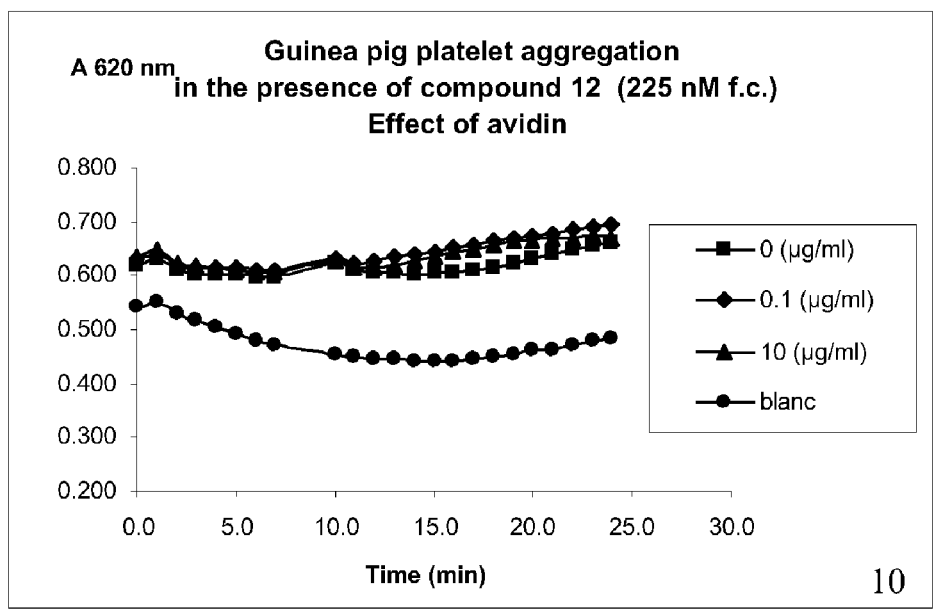

FIG. 3. Effect of avidin on the inhibition of guinea pig platelet aggregation by compound 12 (addition of avidin 9 minutes after ADP-induced platelet aggregation).

Figure 4:
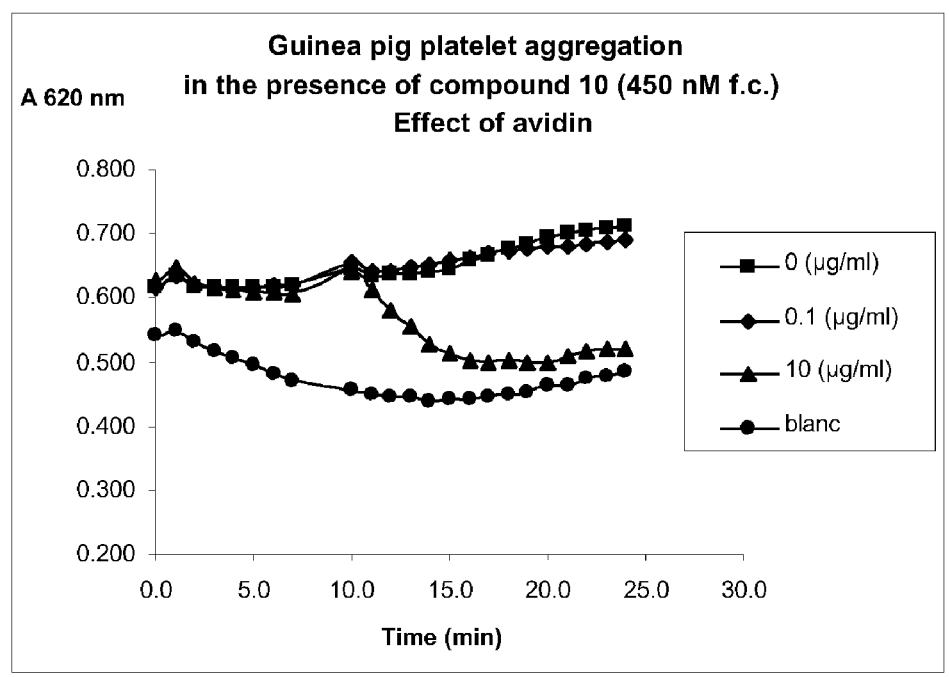

FIG. 4: Effect of avidin on the inhibition of the platelet aggregation by compound 10 (addition of avidin 9 minutes after ADP-induced platelet aggregation).

Figure 5:
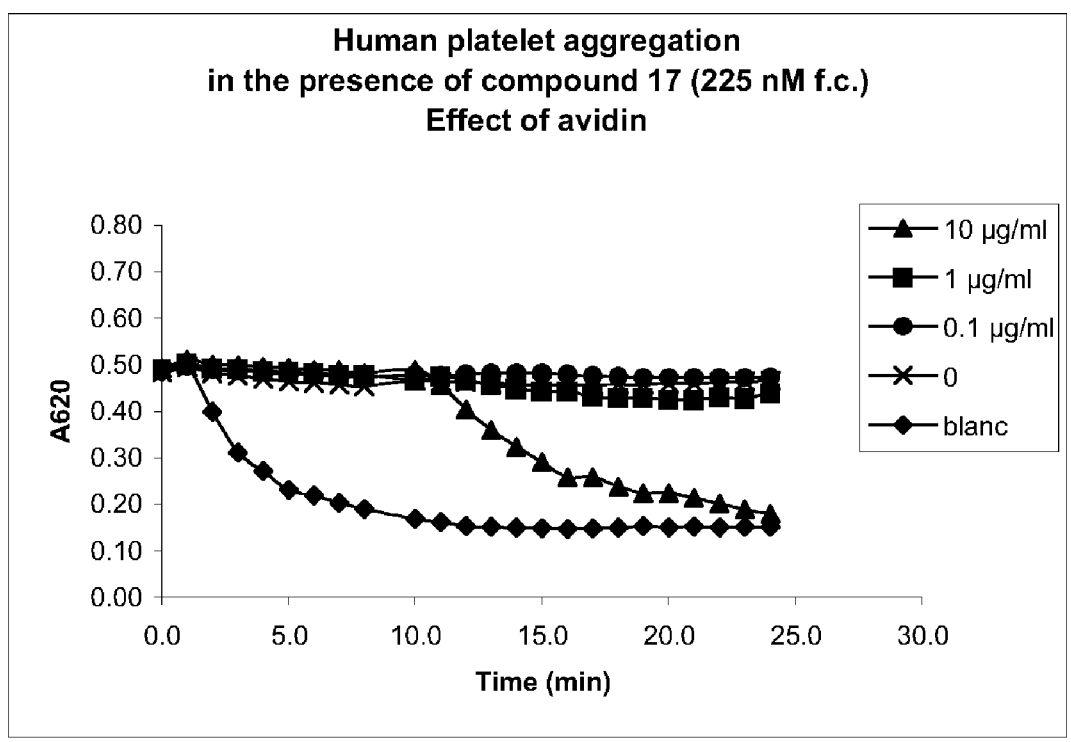

FIG. 5. Effect of avidin on the inhibition of human platelet aggregation by compound 17 (addition of avidin 9 minutes after ADP-induced platelet aggregation).

Figure 6:
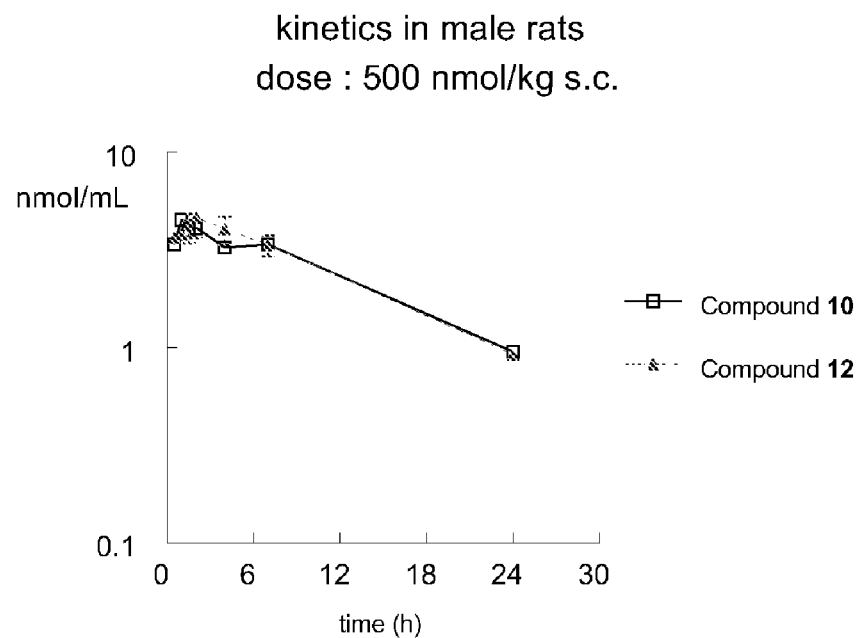

FIG. 6: Shows the mean data after s.c. administration of 500 nmol/kg compound.

Figure 7:
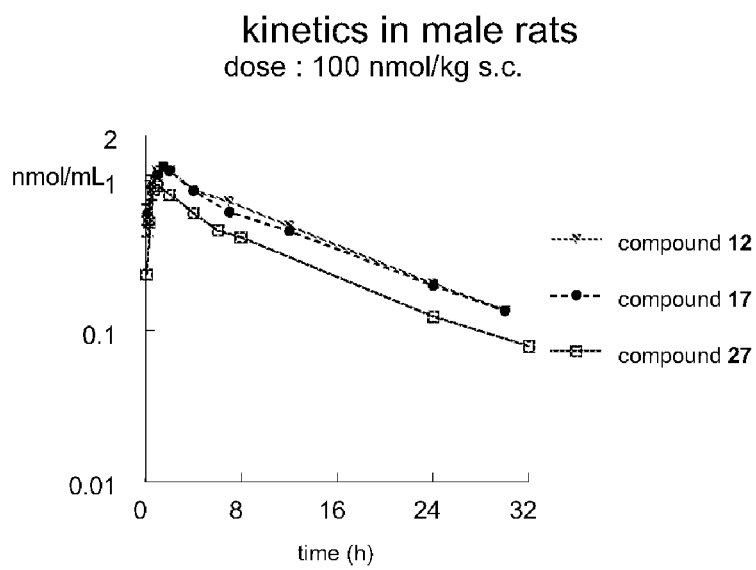

FIG. 7. Mean data after s.c. administration of 100 nmol compound/kg.

Figure 8:
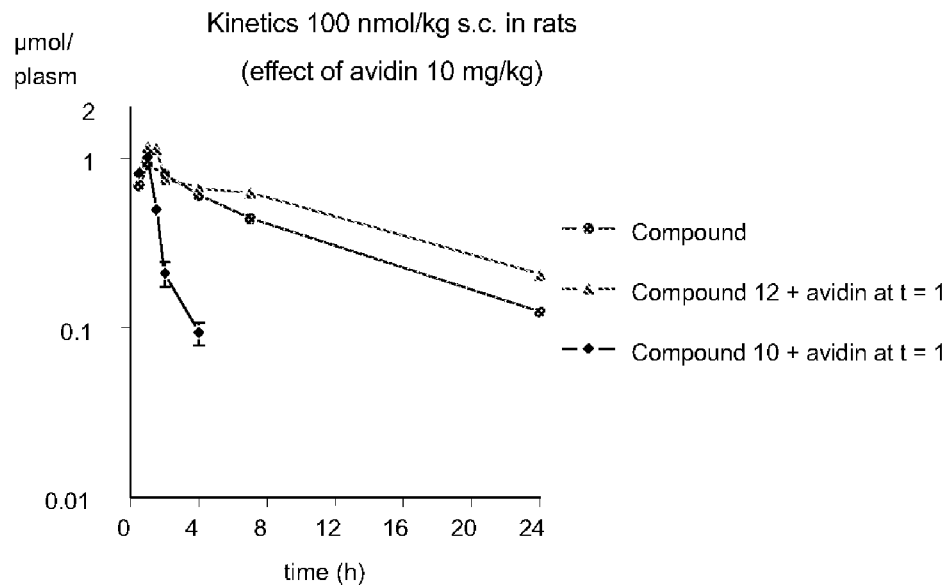

FIG. 8. Shows the mean data after s.c. administration of 100 nmol/kg compound. At t=1 h avidin (10 mg/kg) was administered i.v. to those rats treated with compound 10 or 12. The pharmacokinetic behavior of compound 27 (the pentasaccharide moiety) in the absence of avidin is depicted for comparison.

Figure 9:
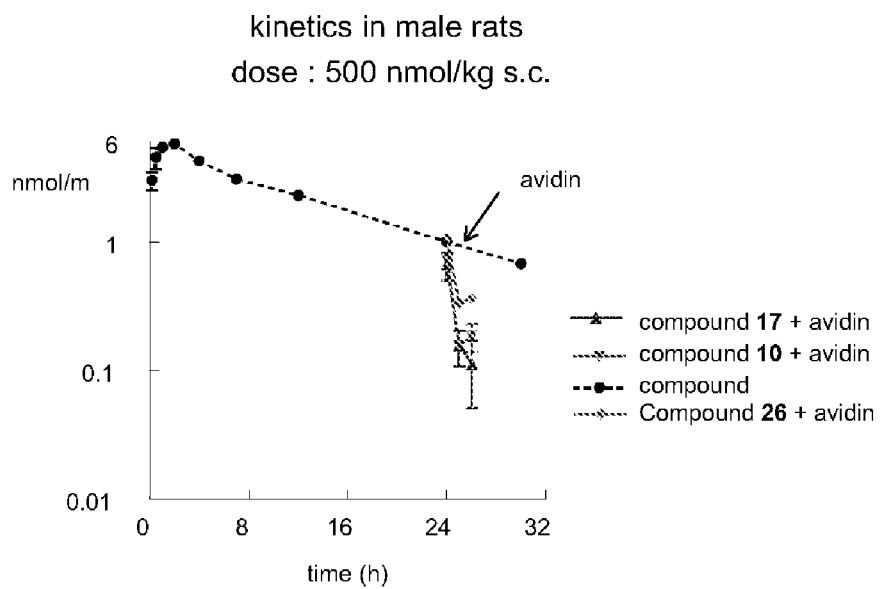

FIG. 9: Mean data after s.c. administration of 500 nmol/kg of compound 10, 17 or 26. At T=24 h avidin (10 mg/kg) was administered i.v. after which blood samples were collected at T=25 and 26 h. For comparison the values of 100 nmol/kg s.c. of compound 17 were normalized to the dose of 500 nmol/kg.

The invention is further illustrated by the following examples.

EXAMPLES

Abbreviations Used

ADP=adenosine 5'-diphosphate
Aq.=aqueous
ATIII=antithrombin III
Bn=benzyl
Boc tert-butyloxycarbonyl
DCM=dichloromethane
DiPEA=N,N-diisopropylethylamine
DMF=N,N-dimethylformamide
fmoc=9-fluorenylmethyl carbamate
NMM=N-methyl morpholine
Me=methyl
sat.=saturated
PRP=platelet rich plasma
PPP=platelet poor plasma
RT=room temperature
TBTU=2-(1H-benzotriazol-1-yl)-1,1,3,3-tetramethyl uronium tetrafluoroborate
TFA=trifluoroacetic acid
THF=tetrahydrofuran
TRAP=thrombin receptor agonist peptide
Z=benzyloxycarbonyl Example 1 tert-Butyl 15-N-(9-fluorenylmethyloxycarbonyl)-15-aza-3,6,9,12-tetraoxa-pentadecanoate (2)

tert-Butyl 15-amino-3,6,9,12-tetraoxa-pentadecanoate (1) (0.50 g, 1.45 mmol), which was prepared as described in EP 1574516, was dissolved in THF (7.5 mL) and H$_2$O (5 mL). 4 N NaOH solution was added until pH was approximately 9. N-9-Fluorenylmethyl carbamate succinimide (FmocOSu, 0.54 g, 1.60 mmol, 1.1 equiv.) was added in portions. After 10 min. additional 4 N NaOH solution was added to adjust the pH to approximately 9. After 3 h the reaction mixture was acidified with 1 N HCl solution to pH 6-7. H$_2$O was added to the reaction mixture which was then extracted 3 times with EtOAc. The organic phase was washed with brine and dried over MgSO$_4$. After filtration the solvent was removed under reduced pressure (50 mbar, 50° C.). The crude oil was purified by silica gel column chromatography (DCM/MeOH, 1/0→95/5, v/v), to give compound 2 as a yellowish oil (0.61 g, 79%). Rf 0.64 (DCM/MeOH, 95/5, v/v).

Example 2

15-N-(9-Fluorenylmethyloxycarbonyl)-15-aza-3,6,9, 12-tetraoxa-pentadecanoate (3)

Compound 2 was dissolved in DCM (3.5 mL) and TFA (3.5 mL) was added under a nitrogen atmosphere. After 1.5 h of stirring the reaction mixture was concentrated under reduced pressure. Then the excess of TFA was removed by repeated concentration in toluene. DCM/Et$_2$O (100 mL, 1/2, v/v) was added and the solution was washed with 1 N HCl. The water layer was extracted with DCM/Et$_2$O (100 mL, 1/2, v/v). The combined organic layers were washed with brine and dried over MgSO$_4$. After filtration the solvent was removed under atmospheric pressure (50° C.). The crude oil was purified by silica gel column chromatography (DCM/MeOH/AcOH, 99/0/1→89/10/1, v/v/v), to give compound 3. Remaining AcOH was removed by dissolving the crude oily product in DCM/Et$_2$O (1/2, v/v) and rinsing with H$_2$O (3×) and brine followed by drying over MgSO$_4$. After filtration the solvent was removed under atmospheric pressure (50° C.) to give compound 3 as a yellowish oil (0.37 g, 67%). Rf 0.32 (DCM/MeOH/AcOH, 89/10/1, v/v).

Example 3 tert-Butyl 15-N-(9-Fluorenylmethyloxycarbonyl)-15-aza-3,6,9,12-tetraoxa-pentadecanoyl-ϵ-N-(benzyloxycarbonyl)-L-lysine (4)

Compound 3 (0.37 mg, 0.77 mmol) was dissolved in DCM (18 mL). DIPEA(0.40 µL, 2.31 mmol, 3 equiv.) and TBTU (0.25 g, 0.77 mmol) were subsequently added under an atmosphere of N$_2$ and the solution was allowed to stir for 10 min. Then ϵ-(Z)-L-Lys-OtBu.HCl (0.29 g, 0.77 mmol) was added and the mixture was stirred for an additional 1.5 h. The reaction mixture was diluted with DCM and rinsed with H$_2$O, 0.1 N HCl, sat. NaHCO$_3$-sol. and brine. The organic phase was dried (MgSO$_4$) and concentrated under atmospheric pressure. Purification was effected by silica gel column chromatography (DCM/MeOH, 1/0→9/1, v/v), to give compound 4 as a yellowish oil (0.51 g, 83%). Rf 0.85 (DCM/MeOH, 9/1, v/v). ESI-MS: 792.6 [M+H]$^+$, 814.6 [M+Na]$^+$, 736.4 [M-tBu+H]$^+$ Example 4 tert-Butyl 15-N-tert-butyloxycarbonyl-15-aza-3,6,9, 12-tetraoxa-pentadecanoyl-ϵ-N-(benzyloxycarbonyl)-L-lysine (5)

Compound 4 (0.26 g, 0.32 mmol) was dissolved in THF (5 mL). Et$_2$NH (1 mL) was added and the solution was allowed to stir for 24 h. The excess Et$_2$N and solvent were removed under reduced pressure (50° C.). Toluene was added and removed under reduced pressure (50° C., 65 mbar) to give N-deprotected product (0.21 g, 0.32 mmol), Rf 0.23 (DCM/MeOH, 9/1, v/v). ESI-MS: 570.4 [M+H]$^+$, 514.4 [M-tBu+H]$^+$.

The crude product was dissolved in DCM (3 mL). Et$_3$N (0.11 mL) was added followed by di-tert-butyl dicarbonate (73 mg, 0.34 mmol, 1.1 equiv.) under an atmosphere of N$_2$. After stirring for 5 h the mixture was added to a cold (5° C.) solution of 0.1 N HCl and extracted with EtOAc. The organic layer was washed with brine and dried (MgSO$_4$). After filtration the solvents were removed under reduced pressure (180 mbar, 50° C.). Purification was effected by silica gel column chromatography (DCM/MeOH, 1/0→95/5, v/v), to give a colorless oil (0.17 g, 82%). Rf 0.5 (DCM/MeOH, 9/1, v/v). ESI-MS: 670.6 [M+H]$^+$, 692.4 [M+Na]$^+$, 570.4 [M-Boc+H]$^+$, 514.1 [M-Boc-tBu+H]$^+$ Example 5

15-aza-3,6,9,12-tetraoxa-pentadecanoyl-ϵ-[D-(+)-biotinyl]-L-lysine (6)

Compound 5 (0.23 g, 0.34 mmol) was dissolved in EtOH (8 mL) and H$_2$O (1.2 mL). After flushing the solution with nitrogen for 5 minutes, Pd/C 10% (0.11 g) was added. Hydrogen was passed trough the solution for 4 h. Nitrogen was flushed trough the solution for 10 minutes to remove all hydrogen. The mixture was filtered over decalite and was concentrated under reduced pressure (170 mbar, 50° C.) to give the N-L-lysine deprotected intermediate as a colorless oil (0.15 g, 81%). Rf 0.02 (DCM/EtOAc, 9/1, v/v).

D-(+)-Biotine (75 mg, 0.31 mmol) was suspended in DCM (7 mL). DiPEA (0.11 mL, 0.62 mmol, 2 equiv.) and TBTU (0.10 g, 0.31 mmol) were subsequently added under an atmosphere of N$_2$ and the solution was allowed to stir for 1 h. A solution of the above described ϵ-N-L-lysine deprotected intermediate in DCM (3 mL) was added to the reaction mixture. The mixture was allowed to stir for 16 h. H$_2$O was added and extracted with DCM (3×). The organic layer was dried (MgSO$_4$), filtered and concentrated under reduced pressure (850 mbar, 50° C.). Purification was effected by silica gel column chromatography (elution: DCM/MeOH, 1/0→9/1 v/v), to give an oil (0.13 g, 60%). Rf 0.48 (DCM/MeOH, 9/1, v/v). ESI-MS: 762.6[M+H]$^+$, 784.6[M+Na]$^+$, 662.4 [M-Boc+H]$^+$, 606.4 [M-Boc-tBu+H]$^+$. The oil was dissolved in a dry 4 N HCl solution in dioxane (4 mL) and stirred. After 1 h an insoluble oil appeared after which the solvent was removed under reduced pressure (100 mbar, 50° C.). to give compound 6 in quantitative yield. ESI-MS: 606.4 [M+H]$^+$, 628.4 [M+Na]$^+$.

Example 6

Benzyl N-<3-{[-ϵ-(D-(+)-biotinyl)-L-lysine-15-aza-3,6,9,12-tetraoxa-pentadecanoyl]-carbonyl}-benzenesulfonyl>-4-O-{4-(N-benzyloxycarbonyl-4-piperidinyl)-butyl}-L-tyrosine (8)

Compound 7 (0.10 g, 0.16 mmol), which was prepared as described in EP 1574516, was dissolved in DMF (4 mL). DIPEA(56 µL, 0.32 mmol, 2 equiv.) and TBTU (51 mg, 0.16 mmol) were subsequently added under an atmosphere of N$_2$ and the solution was allowed to stir for 45 minutes. Compound 6 (0.17 mmol) was dissolved in DMF (1 mL), DiPEA (28 µL, 0.16 mmol, 1 equiv.) and added to the reaction mixture. The mixture was allowed to stir for 16 h. The reaction mixture was diluted with DCM and washed with 1 N HCl solution. The organic phase was washed with H$_2$O (3×), dried (MgSO$_4$), filtered and concentrated under reduced pressure (850 mbar, 50° C.). Purification was effected by silica gel column chromatography (elution: DCM/MeOH/AcOH, 99/0/1→79/20/1 v/v), to give compound 8 (56 mg, 27%). Rf 0.15 (DCM/MeOH, 9/1, v/v). ESI-MS: 1316.6 [M+H]$^+$, 1338.8 [M+Na]$^+$, 1182.6 [M-Z+H]$^+$, 1204.6 [M-Z+Na]$^+$. 1314.8 [M-H]$^+$

Example 7

General Procedure for Preparation of Compounds 10, 12, 17 and 26

The carboxylic acid derivative (33 µmol) (i.e. compound 8, 11, 16 or 25) was dried by repeated concentration in dry DMF (2×2 mL), dissolved in DMF (1 mL) and stirred in the presence of TBTU (11 mg, 33 µmol) and DiPEA (5.7 µL, 33 µmol), under an atmosphere of $N_2$. After 1 h, pentasaccharide 9 (31 µmol) was added. The reaction mixture was stirred overnight at RT and analyzed by ion exchange (Mono-Q) and reversed phase (Luna C18) chromatography. The reaction mixture was concentrated (<50° C., 15 mmHg). The (crude) product (10 mg/mL in $H_2O$/t-BuOH, 1/1, v/v) was deprotected by hydrogenation ($H_2$) over 10% Pd/C (an equal amount in weight was added with respect to the crude product). After 16 h the solution was degassed, filtered over a 0.45 µM HPLC filter and concentrated under reduced pressure (<50° C., 15 mm Hg). The conjugate was purified by ion exchange chromatography (Q-sepharose, buffer: $H_2O \rightarrow 2M$ NaCl), followed by desalting with a Sephadex G25-column ($H_2O$) and lyophilization.

Example 8

Methyl O-2,3-di-O-methyl-4-O-<<<12-N-<<$N^\epsilon$-(D-(+)-biotinyl)-N-<3-{[15-N-(15-aza-1-keto-3,6,9,12-tetraoxa-pentadecyl)]-carbonyl}-benzenesulfonyl>-4-O-{4-(4-piperidinyl)-butyl}-L-tyrosyl>-lysyl>>-12-aza-3,6,9-trioxa-dodecyl>>>-6-O-sulfo-alpha-D-glucopyranosyl-(1->4)-O-2,3-di-O-methyl-beta-D-glucopyranuronosyl-(1->4)-O-2,3,6-tri-O-sulfo-alpha-D-glucopyranosyl-(1->4)-O-2,3-di-O-methyl-alpha-L-idopyranuronosyl-(1->4)-2,3,6-tri-O-sulfo-alpha-D-glucopyranoside nonakis sodium salt (10)

Conjugation of carboxylic acid 8 (37.8 mg, 28.7 µmol) to pentasaccharide 9 (51.7 mg, 27.4 µmol) [which may be obtained by coupling of the derivatised monosaccharide 5 described in WO 01/42262 with the tetrasaccharide 48 described in US 2004/0024197 using methods similar to those described in these patent applications, including deprotection and sulfation], followed by purification and deprotection was effected according to the general procedure. Conjugate 10 was obtained as a white solid, yield 13.6 mg (16%, 2 steps).

$^1$H-NMR ($D_2O$, 600 MHz, HH-COSY): δ 7.85 (d, 1H), 7.78 (d, 1H), 7.63 (d, 1H), 7.42 (t, 1H), 6.85 (d, 1H), 6.50 (d, 1H), 5.39 (d, 1H), 5.33 (d, 1H), 5.13 (bs, 1H), 5.08 (d, 1H), 4.58 (m, 1H), 4.58 (d, 1H), 4.49 (m, 1H), 4.48 (m, 1H), 4.33 (m, 1H), 4.29 (m, 1H), 4.28 (dd, 1H), 4.22 (dd, 1H), 4.21 (m, 2H), 4.20 (m, 1H), 4.17 (m, 2H), 4.09 (m, 1H), 4.07 (m, 1H), 4.05 (d, 1H), 4.02 (m, 1H), 3.96 (s, 2H), 3.89 (m, 1H), 3.86 (m, 1H), 3.85 (m, 2H), 3.79 (m, 2H), 3.73 (m, 1H), 3.69 (m, 1H), 3.65 (m, 1H), 3.61-3.51 (m, 26H), 3.60-3.38 (8xs, 34H), 3.48 (m, 2H), 3.42 (m, 1H), 3.38 (m, 1H), 3.32 (m, 1H), 3.19 (m, 3H), 2.92-2.2.89 (m, 1H), 2.67 (d, 1H), 2.48 (m, 1H), 2.13 (t, 2H), 1.91 (d, 1H), 1.70 (m, 2H), 1.65-1.37 (m, 5H).

ESI-MS: found: m/z 1381.3 $[M+H]^{2-}$, 1392.3 $[M+Na]^{2-}$, 1402.8 $[M+2Na]^{2-}$, 1413.8 $[M+3Na]^{2-}$, 920.2 $[M-3H]^{3-}$, 927.5 $[M-3H+Na]^{3-}$, 934.5 $[M-3H+2Na]^{3-}$, 690.2 $[M-4H]^{4-}$, 694.7 $[M-4H+Na]^{4-}$

Example 9

Methyl O-2,3-di-O-methyl-4-O-<<<12-N-<3-{[15-N-(15-aza-1-keto-3,6,9,12-tetraoxa-pentadecyl)]-carbonyl}-benzenesulfonyl>-4-O-{4-(4-piperidinyl)-butyl}-L-tyrosyl>-12-aza-3,6,9-trioxa-dodecyl>>-6-O-sulfo-alpha-D-glucopyranosyl-(1->4)-O-2,3-di-O-methyl-beta-D-glucopyranuronosyl-(1->4)-O-2,3,6-tri-O-sulfo-alpha-D-glucopyranosyl-(1->4)-O-2,3-di-O-methyl-alpha-L-idopyranuronosyl-(1->4)-2,3,6-tri-O-sulfo-alpha-D-glucopyranoside nonakis sodium salt (12)

Compound 12 was obtained by coupling of compound 9 (101 mg, 53.9 µmol) with compound 11 (60.0 mg, 56.6 µmol), which was prepared as described in EP 1574516, according to the general procedure. Yield 72 mg (52%).

$^1$H-NMR ($D_2O$, 600 MHz, HH-COSY): δ 7.84 (m, 1H), 7.75 (m, 1H), 7.62 (m, 1H), 7.42 (t, 1H), 6.83 (d, 2H), 6.48 (d, 2H), 5.38 (d, 1H), 5.33 (m, 1H), 5.08 (d, 1H), 5.02 (bs, 1H), 4.58 (d, 1H), 4.46 (bs, 2H), 4.28 (m, 2H), 4.17 (m, 1H), 4.22 (m, 1H), 4.20 (m, 2H), 4.11 (m, 2H), 4.04 (d, 1H), 4.03 (m, 1H), 4.02 (m, 1H), 3.88 (m, 2H), 3.84 (m, 2H), 3.82 (m, 1H), 3.79 (m, 1H), 3.72 (1H, m), 3.66 (m, 2H), 3.62-3.33 (m, 54H), 3.20 (dd, 1H), 3.18 (m, 1H), 2.92 (m, 2H), 1.92 (m, 2H), 1.70 (m, 2H), 1.58 (m, 1H), 1.44 (m, 2H), 1.33 (m, 4H). ESI-MS: m/z 1225.2 $[M+5H+2Na]^{2-}$, 823.8 $[M+3Na+3H]^{3-}$, 816.5 $[M+2Na+4H]^{3-}$, 809.1 $[M+Na+5H]^{3-}$.

Example 10

[D-(+)-biotinyl]-L-aspartate alpha-benzyl ester (14)

To a suspension of D-Biotin (2.0 g, 8.19 mmol) in DMF (52 mL) was added pentafluorophenol (1.6 g, 15.6 mmol) followed by DCC (2.5 g, 12.3 mmol). The reaction mixture was allowed to stir, under nitrogen atmosphere, overnight at RT. The reaction mixture remained a suspension and was filtered off and concentrated. The residue was taken up into $Et_2O$ and stirred for several minutes after which the suspension was filtered an dried und vacuum to give a white solid (2.58 g) ESI-MS: 411 $[M+H]^+$. The solid was dissolved in DMF (90 mL) and $Et_3N$ (1.24 mL, 8.82 mmol, 1.4 equiv.) was added. H-Asp-OBn was added in portions as a solid. After approximately 15 min the reaction mixture became clear and an additional 2 h stirring was allowed. The reaction mixture was concentrated under reduced pressure and water was added followed by MeOH (3:1). The solid formed was filtered off, washed with $Et_2O$ and dried under vacuum to give compound 14 as a white solid (2.92 g, 77%) ESI-MS: 450 $[M+H]^+$.

Example 11

N-15-Aza-3,6,9,12-tetraoxa-pentadecanoyl-ε-<N-[D-(+)-biotinyl]-L-aspartyl alpha-benzyl ester>-L-lysine (15)

Compound 13 (3.60 g, 6.72 mmol, 1.07 equiv.), which was obtained as described above for the synthesis of compound 6, and compound 14 (2.92 g, 6.30 mmol) were dissolved in DMF (80 mL). DiPEA (2.2 mL, 12.6 mmol, 2 equiv.) was added, under nitrogen atmosphere, followed by TBTU (2.53 g, 7.88 mmol, 1.25 equiv.). The reaction mixture was allowed to stir overnight, after which the solvent was removed under reduced pressure. Purification was accomplished using HPLC (ACN/$H_2O$) to give a yellowish oil (2.31 g). ESI-MS: 967 $[M+H]^+$. Deprotection was carried out in DCM/TFA (1:1, 60 mL) while stirring for 2 h at RT. DCM was added (150 mL) and solvents were removed by heating (45° C., atmospheric pressure). This process was repeated 3× and was followed by repeated concentration in toluene (3×). Compound 15 was collected as a yellowish solid (3.29 g, 30%). ESI-MS: 811 [M+H]$^+$ Example 12

ε-N-(D-(+)-biotinyl-beta-L-aspartyl)-N-<3-{[15-N-(15-aza-1-keto-3,6,9,12-tetraoxa-pentadecyl)]-carbonyl}-benzenesulfonyl>-4-O-{4-(4-piperidinyl)-butyl}-L-tyrosyl>-L-lysine (16)

To a solution of 7 (1.41 g, 1.94 mmol) in DMF (50 mL), DiPEA (1.0 mL, 5.8 mmol, 3 equiv.) was added, under nitrogen atmosphere, followed by TBTU (685 mg, 2.1 mmol, 1.1 equiv.) and allowed to stir for 1 h. Then a solution of 15 in DMF (20 mL) was added and stirred for 3 h. The reaction mixture was concentrated under reduced pressure and the crude product was purified by HPLC (ACN/H$_2$O/TFA) to give a yellowish solid (783 mg, 26%). ESI-MS: 1522 [M+H]$^+$ Example 13

Methyl 2,3-di-O-methyl-4-O-<<<12-N-<<ε-N-(D-(+)-biotinyl-beta-L-aspartyl)-N-<3-{[15-N-(15-aza-1-keto-3,6,9,12-tetraoxa-pentadecyl)]-carbonyl}-benzenesulfonyl>-4-O-{4-(4-piperidinyl)-butyl}-L-tyrosyl>-L-lysyl>>-12-aza-3,6,9-trioxa-dodecyl>>>-6-O-sulfo-alpha-D-glucopyranosyl-(1->4)-O-2,3-di-O-methyl-beta-D-glucopyranuronosyl-(1->4)-O-2,3, 6-tri-O-sulfo-alpha-D-glucopyranosyl-(1->4)-O-2,3-di-O-methyl-alpha-L-idopyranuronosyl-(1->4)-2,3,6-tri-O-sulfo-alpha-D-glucopyranoside decakis sodium salt (17)

The synthesis of compound 17 was basically achieved according to the general procedure. Thus, to a solution of 16 (768 mg, 0.505 mmol) in DMF (50 mL), DiPEA (106 μL, 0.61 mmol, 1.2 equiv.) was added, followed by TBTU (178 mg, 0.56 mmol, 1.1 equiv.) under nitrogen. After stirring the solution for 1 h compound 9 (906 mg, 0.48 mmol) was added and stirring was continued for 16 h. The reaction mixture was concentrated under reduced pressure and purified on Q-sepharose (H$_2$O→2M NaCl). Desalting was carried out on Sephadex-G25 to give a clear oil (1.5 g). The oil was dissolved in H$_2$O (37 mL) and t-BuOH (37 mL), and 10% Pd/C (670 mg) was added under an atmosphere of nitrogen. Hydrogen was lead trough the solution for 16 h. After removing the Pd/C catalyst by filtration the compound was again purified on Q-sepharose and desalted on Sephadex-G25 to give compound 17 in a yield of 465 mg (34%).

$^1$H-NMR (D$_2$O, 600 MHz, HH-COSY): δ 7.94 (m, 1H), 7.86 (t, 1H), 7.71 (m, 1H), 7.52 (t, 1H), 6.93 (d, 1H), 6.58 (d, 1H), 5.45 (d, 1H), 5.42 (d, 1H), 5.18 (bs, 1H), 5.15 (d, 1H), 4.56 (m, 1H), 4.33-4.41 (m, 2H), 4.30-4.21 (m, 4H), 4.13-4.05 (m, 4H), 3.89-3.96 (m, 5H), 3.87-3.82 (m, 3H), 3.81-3.70 (m, 7H), 3.69-3.60 (m, 39H), 3.59-3.48 (m, 13H), 3.47-3.35 (m, 8H), 3.30-3.24 (m, 3H), 3.11 (t, 2H), 3.06-2.93 (m, 4H), 2.79-2.73 (m, 2H), 2.60-2.52 (m, 2H), 2.26 (t, 2H), 2.01-1.96 (m, 2H), 1.81-1.74 (m, 3H), 1.71-1.25 (m, 20H). ESI-MS: m/z 1481.9 [M+4Na–4H]$^{2-}$, 1471.0 [M+3Na–3H]$^{2-}$, 980.7 [M+3Na–3H]$^{3-}$M+Na+5H]$^{3-}$

Example 14

ε-N-Methyl-ε-N-trifluoroacetyl-L-lysine (19)

Compound 18 (1.26 g, 3.2 mmol) was dissolved in DMF (15 mL) and K$_2$CO$_3$ (2.2 g, 16 mmol, 5 equiv.) was added followed by methyl iodide (1.6 mL, 25.6 mmol, 8 equiv.). The solution was heated to 100° C. and stirred for 24 h in a sealed flask. The reaction mixture was cooled and diluted with EtOAc. The resulting solid was filtered, washed with brine and dried on MgSO$_4$. The crude product was purified by silica gel column chromatography (DCM/MeOH, 95/5) to give an oil (1.18 g) which was dissolved in a mixture of DCM (5 mL) and TFA (5 mL) and which was stirred for 1 h. Then the solvents were removed under reduced pressure and the crude product was concentrated in toluene (3×) to yield compound 19 (1.57 g, 87%) ESI-MS: m/z 271.2 [M+H]$^+$ Example 15

Methyl 15-azido-3,6,9,12-tetraoxa-pentadecanoyl-ε-N-methyl-ε-N-trifluoroacetyl-L-lysine (21)

Compound 19 (1.57 g, 2.16 mmol) and 20 (0.60 g, 2.16 mmol), which was prepared by deprotection of the corresponding tert-butyl ester derivative described in EP 1574516, were coupled as described for the synthesis of compound 4 to give compound 21 in a yield of 86% (980 mg, 1.85 mmol). ESI-MS: m/z 530.2 [M+H]$^+$, 552.2 [M+Na]$^+$ Example 16

15-Azido-3,6,9,12-tetraoxa-pentadecanoyl-ε-N-methyl-L-lysine (22)

Compound 21 (0.98 g, 1.85 mmol) was dissolved in THF (6 mL), 1 N LiOH (6 mL) was added and the resulting solution was stirred for 2 h at RT. The reaction mixture was neutralized by addition of 1 N HCl and was subsequently concentrated under reduced pressure to yield the crude deprotected compound 22 which was used without further purification in the next reaction. ESI-MS: m/z 420.2 [M+H]$^+$ Example 17

15-Azido-3,6,9,12-tetraoxa-pentadecanoyl-ε-N-[D-(+)-biotinyl]-εN-methyl-L-lysine (23)

Compound 22 (1.85 mmol, crude) was coupled to D-(+)-biotin (0.54 g, 2.22 mmol, 1.2 equiv.) as described above for the preparation of compound 6 to give the biotinylated lysine derivative 23 which was used without purification in the next reaction. ESI-MS: m/z 646.4 [M+H]$^+$, 668.6 [M+Na]$^+$ Example 18

15-Aza-3,6,9,12-tetraoxa-pentadecanoyl-ε-N-[D-(+)-biotinyl]-εN-methyl-L-lysine (24)

Compound 23 (1.85 mmol, crude) was dissolved in t-BuOH (50 mL) and H$_2$O (50 mL). 10% Pd/C (750 mg) was added under nitrogen atmosphere. Hydrogen was led through the solution for approximately 4 h. Pd/C was removed by filtration over Decalite and washed with EtOH. The solvents were removed under reduced pressure (50 mbar, 50° C.) to give crude compound 24 as an oil (>100%, residual solvent). ESI-MS: m/z 620.4 [M+H]$^+$

Example 19

Benzyl N-<3-{[-ε-(D-(+)-biotinyl-ε-N-methyl)-L-lysine-15-aza-3,6,9,12-tetraoxa-pentadecanoyl]-carbonyl}-benzenesulfonyl>-4-O-{4-(N-benzyloxycarbonyl-4-piperidinyl)-butyl}-L-tyrosine (25)

Coupling of compound 24 (0.58 g, 0.93 mmol, crude) to compound 7 (0.50 g, 0.68 mmol) was performed as described above for the synthesis compound 8. Purification by silica gel column chromatography and preparative HPLC gave the ε-N-methylated lysine derivative 25 in a yield of 77 mg (8.5% over the last four steps starting with compound 21). ESI-MS: m/z 1330.6 [M+H]$^+$

Example 20

Methyl O-2,3-di-O-methyl-4-O-<<<12-N-<<N-(D-(+)-biotinyl-ε-N-methyl)-N-<3-{[15-N-(15-aza-1-keto-3,6,9,12-tetraoxa-pentadecyl)]-carbonyl}-benzenesulfonyl>-4-O-{4-(4-piperidinyl)-butyl}-L-tyrosyl>-lysyl>>-12-aza-3,6,9-trioxa-dodecyl>>>>-6-O-sulfo-alpha-D-glucopyranosyl-(1->4)-O-2,3-di-O-methyl-beta-D-glucopyranuronosyl-(1->4)-O-2,3,6-tri-O-sulfo-alpha-D-glucopyranosyl-(1->4)-O-2,3-di-O-methyl-alpha-L-idopyranuronosyl-(1->4)-2,3,6-tri-O-sulfo-alpha-D-glucopyranoside nonakis sodium salt (26)

Compound 25 (77 mg, 58 μmol) was coupled to pentasaccharide derivative 9 (0.10 g, 55 μmol) as described in the general procedure. Purification and desalting of the crude product as described in the general procedure was followed by lyophilization to give target conjugate 26 in a yield of 50 mg (27%). ESI-MS: m/z 2762.5 [M+H]$^+$

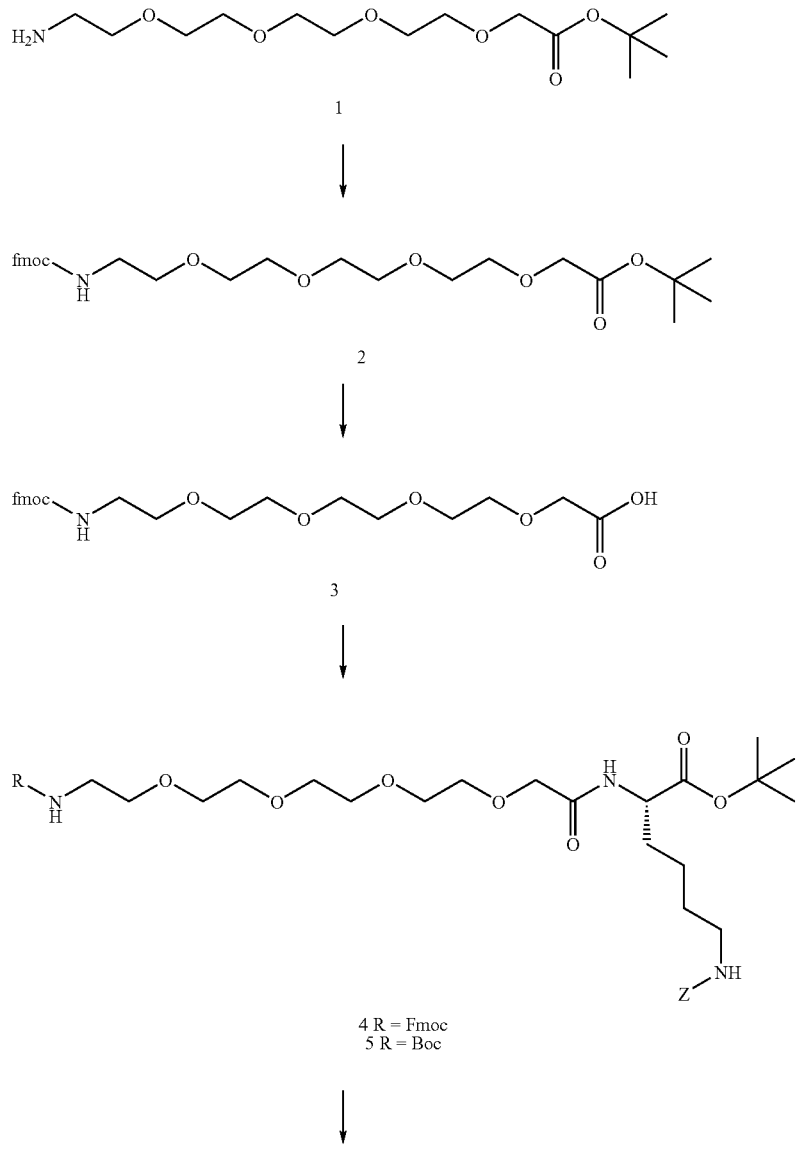

Scheme 1a

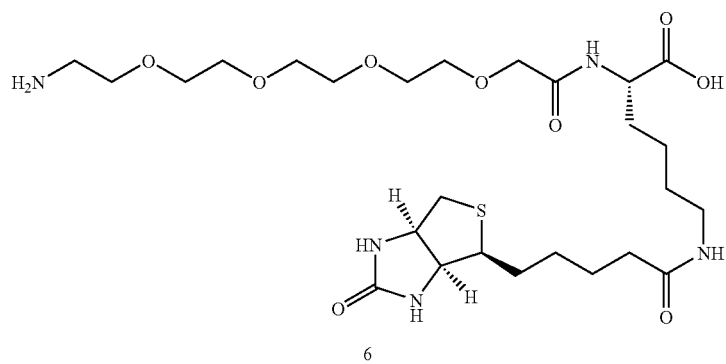
6
Scheme 1b
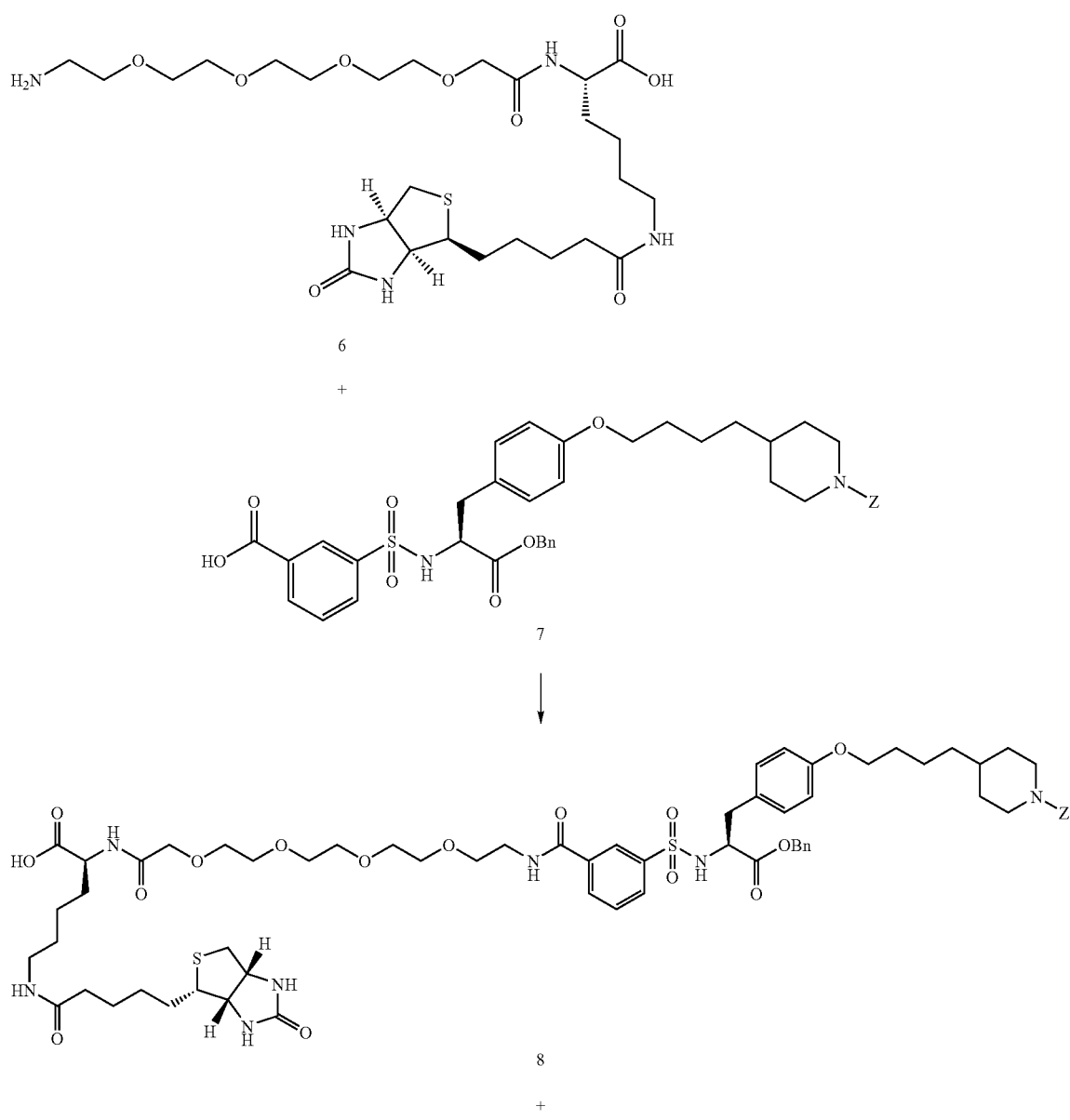
6
+
7
8
+

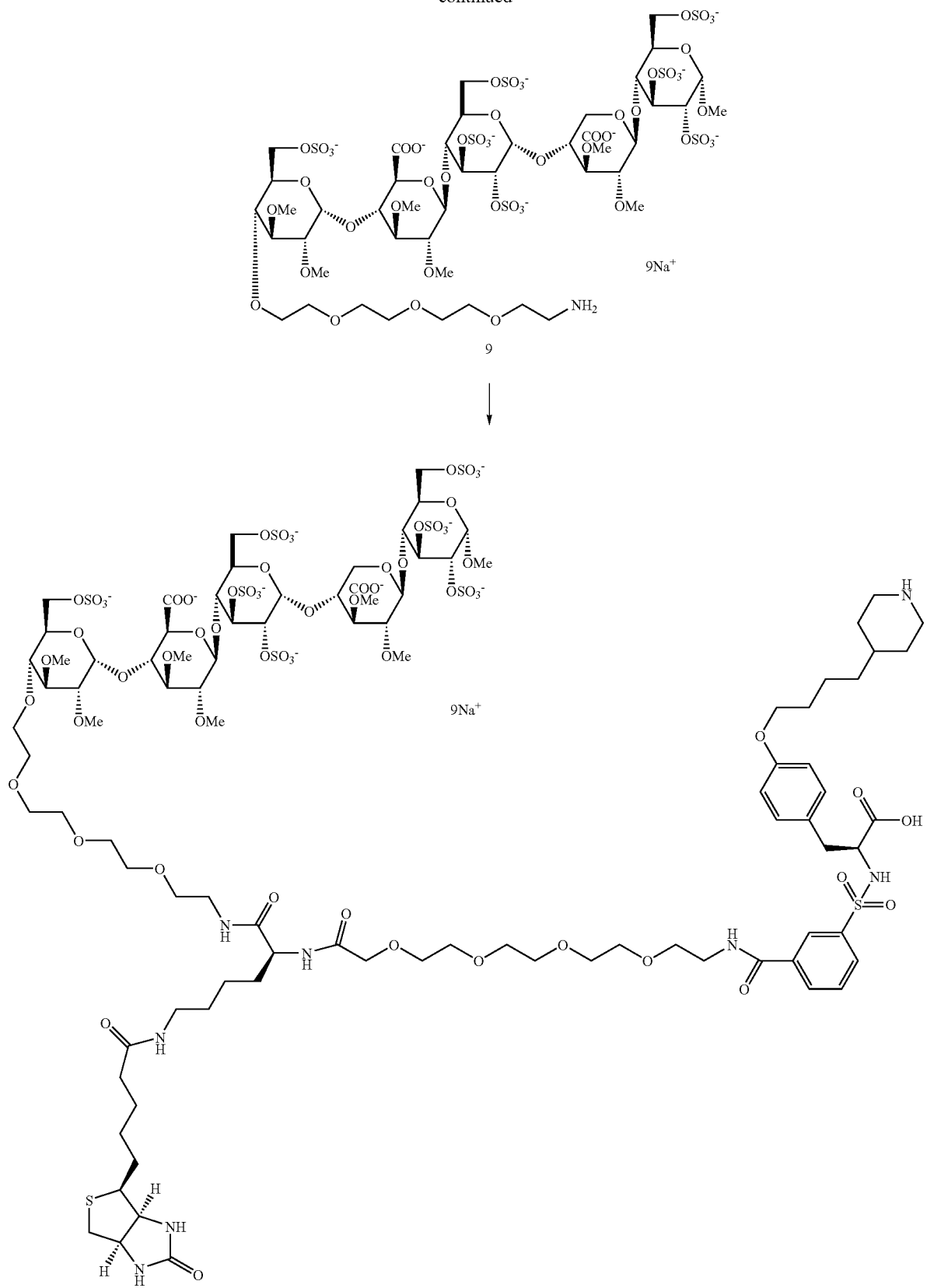

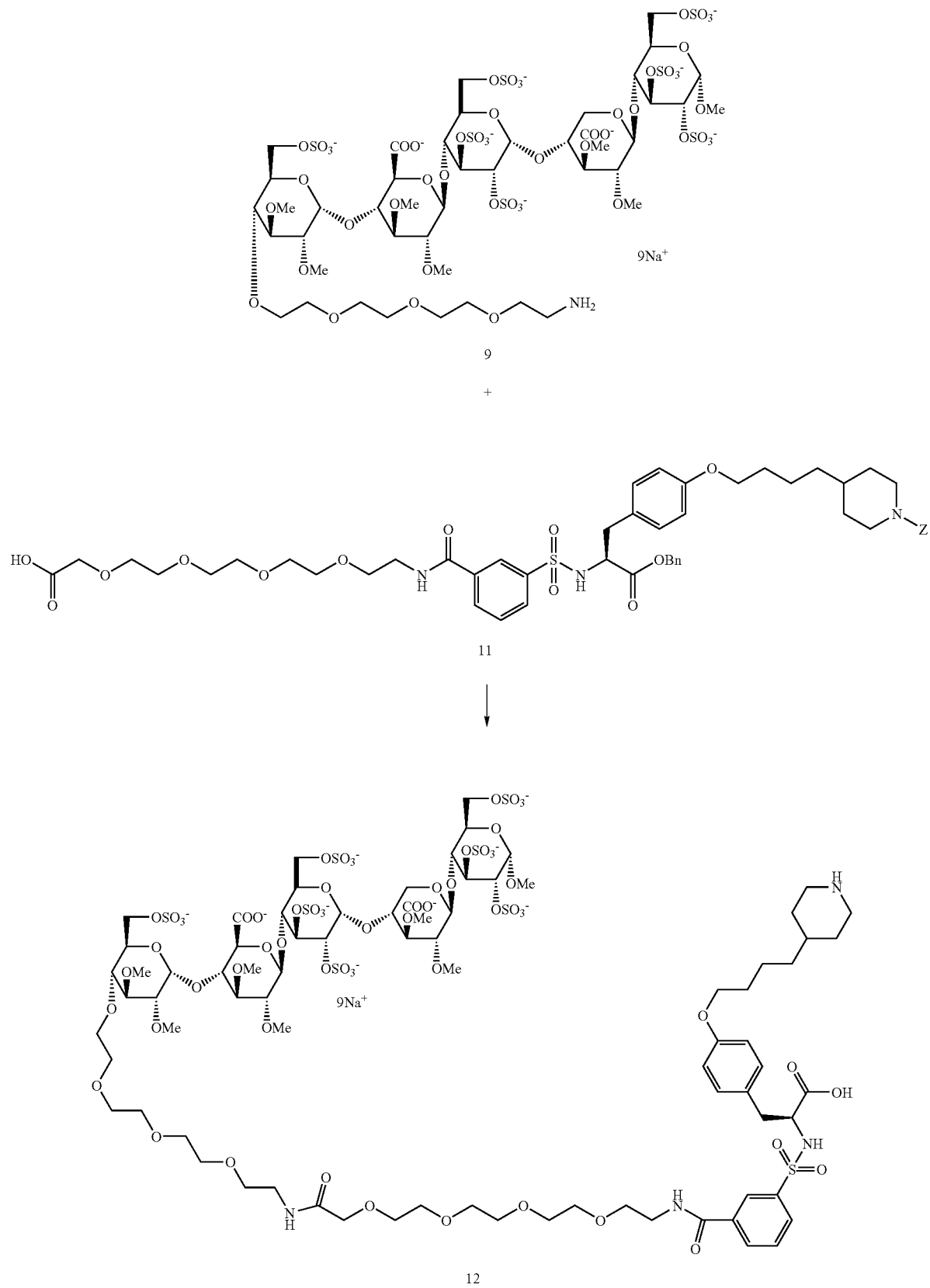

Scheme 3a
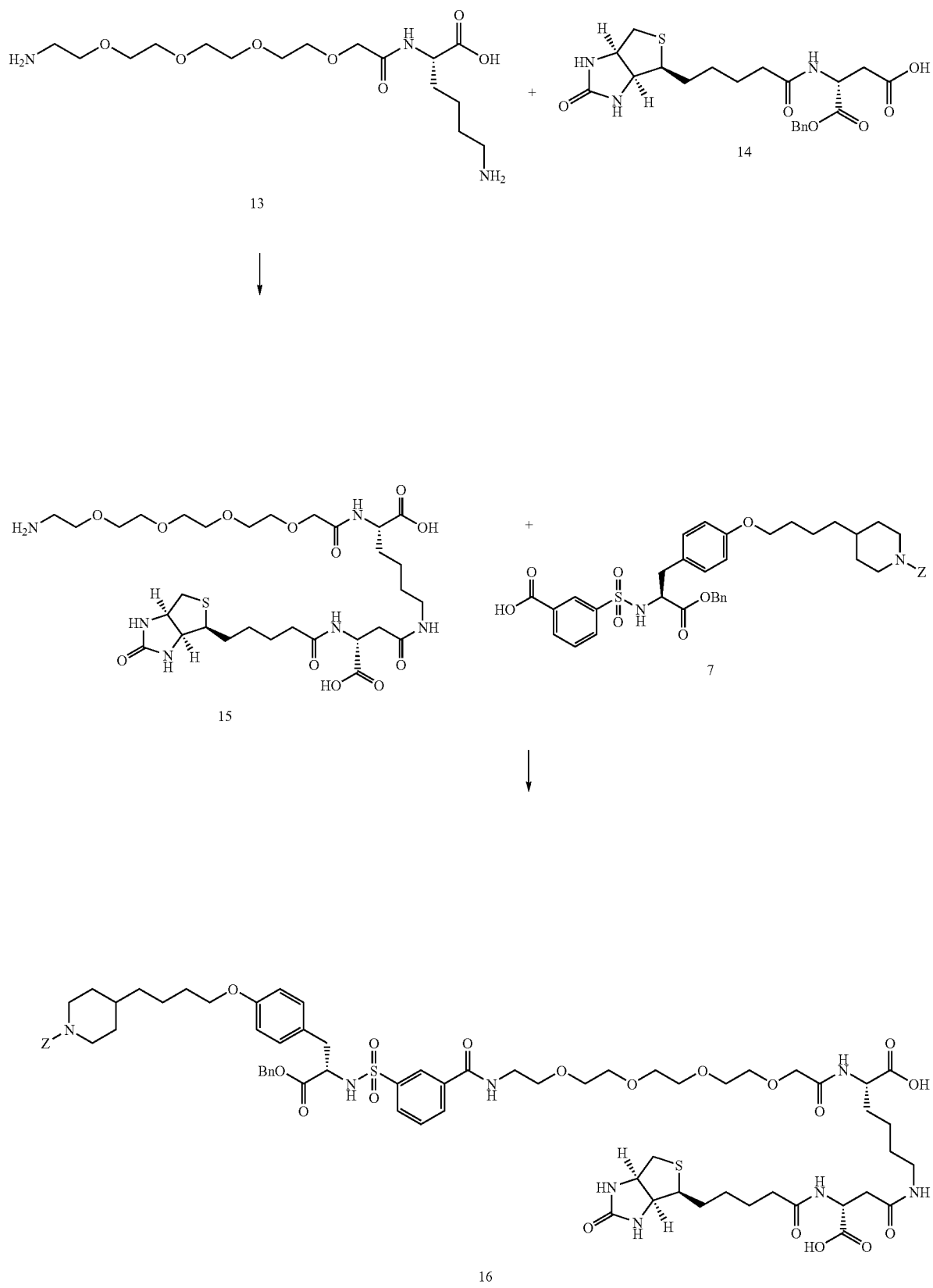

31 32
Scheme 3b
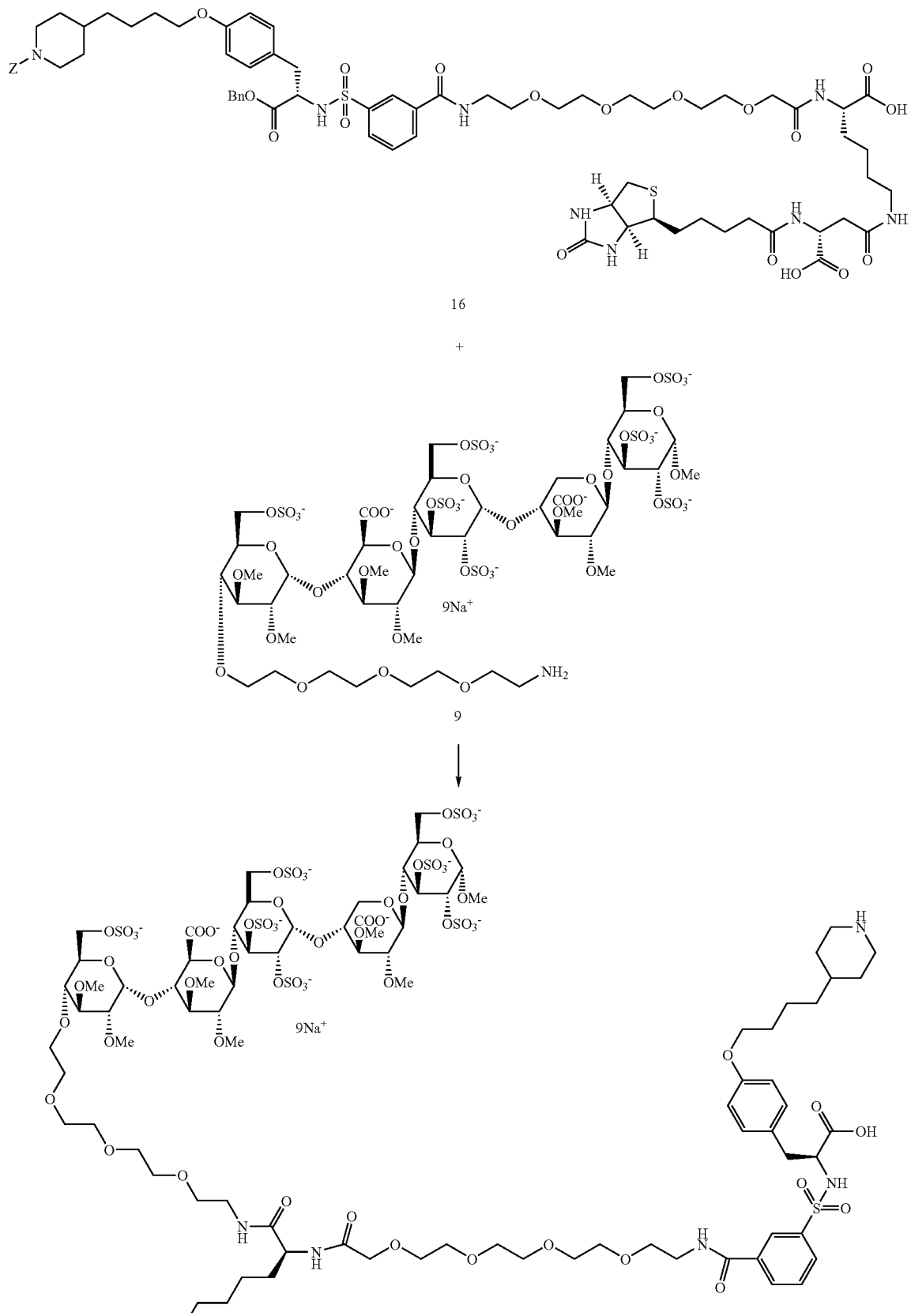

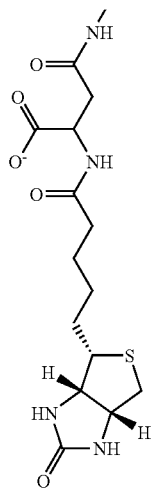
Scheme 4a
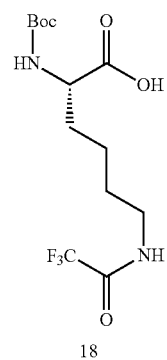
18
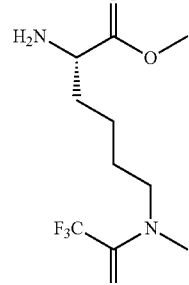
19
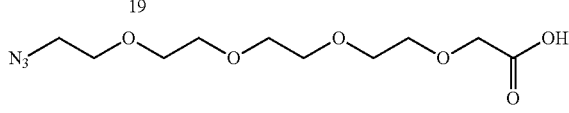
20
21
22

35
-continued
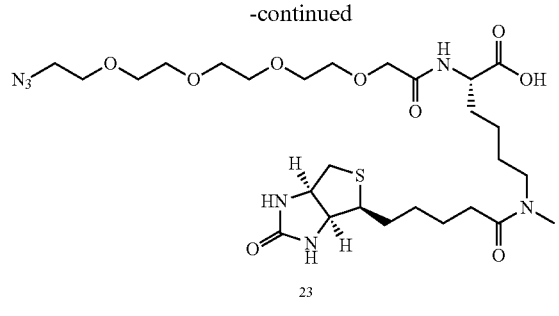
23
36
-continued
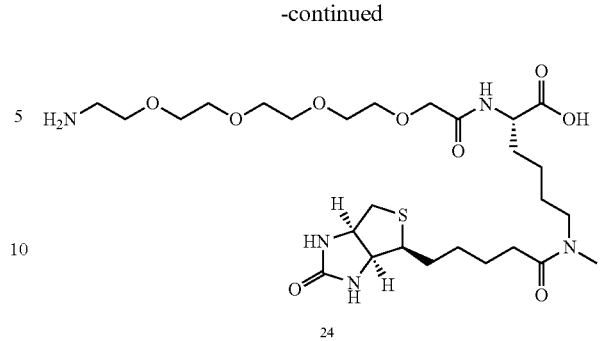
24
Scheme 4b
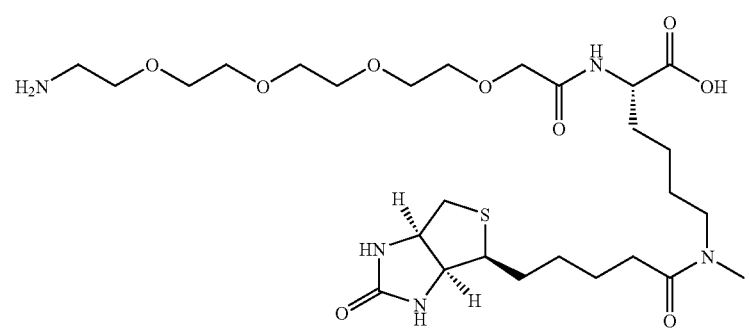
24
+
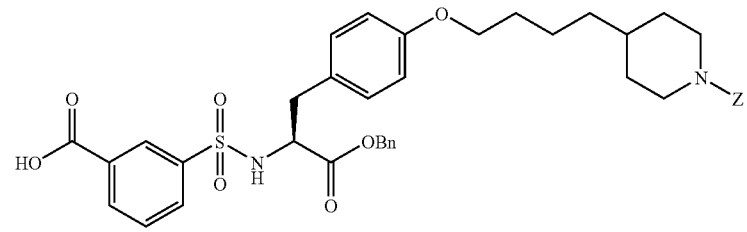
7
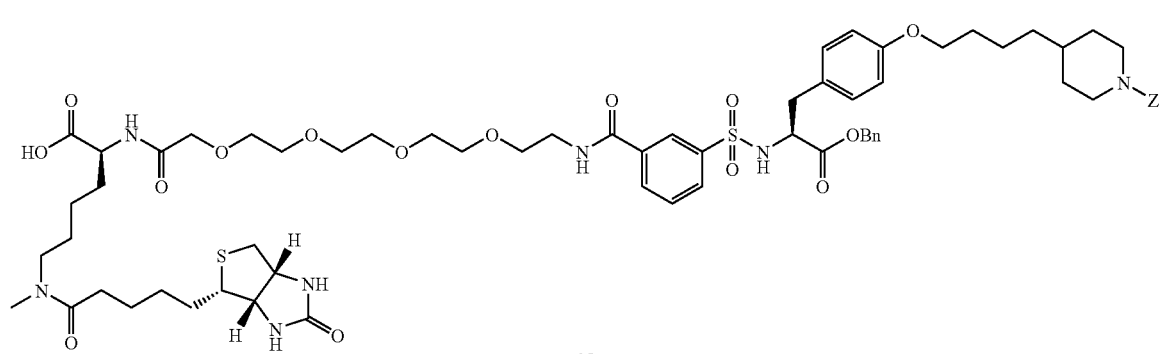
25
+

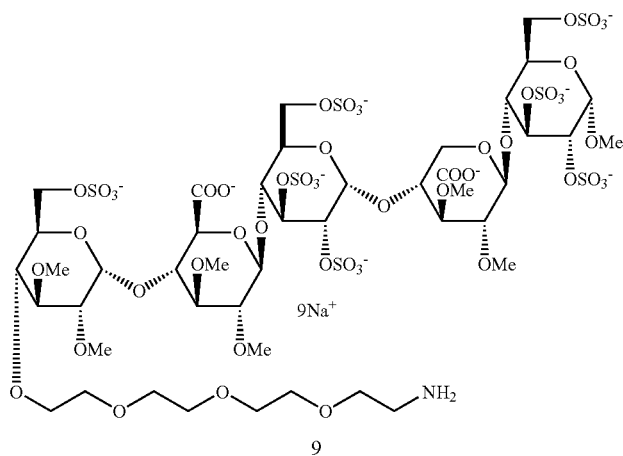
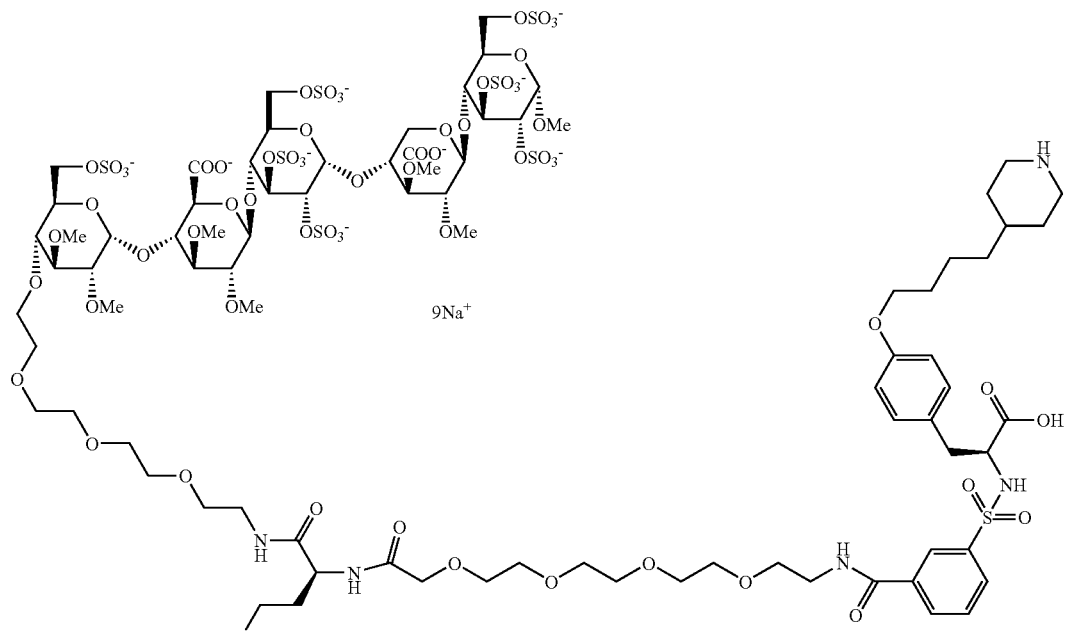
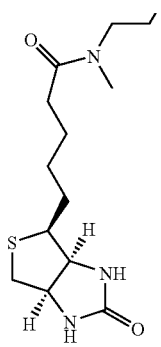

Reference Compounds

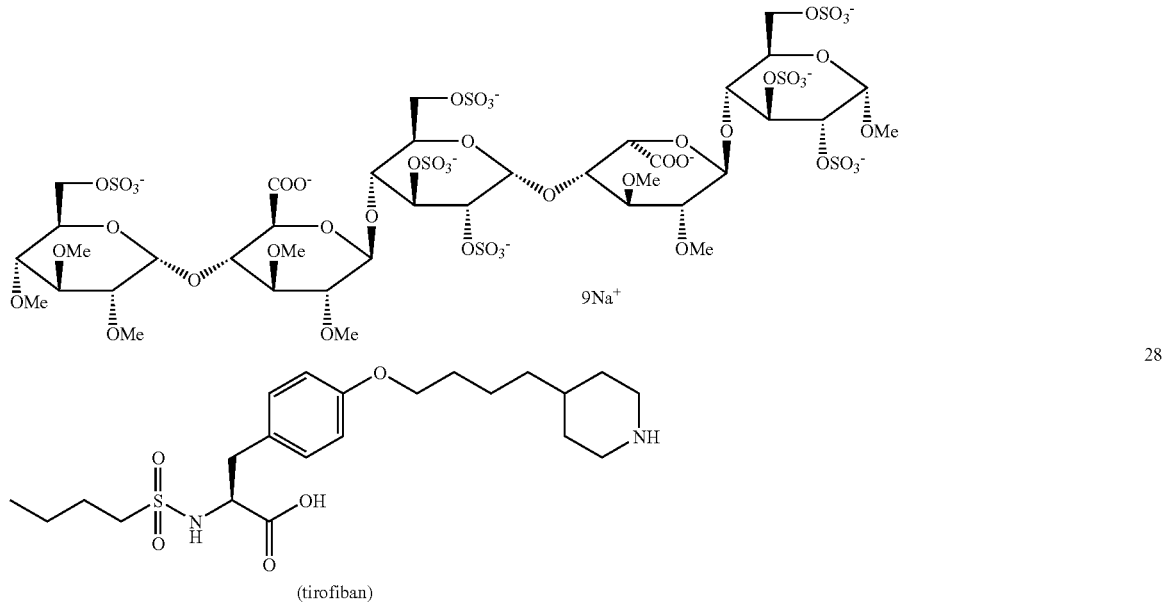

(tirofiban)

Example 21

Pharmacology 1.1 In Vitro Test for Inhibition of Guinea Pig Platelet Aggregation Induced by ADP Addition of adenosine diphosphate (ADP) to human or guinea pig platelet rich plasma (PRP) in vitro induces platelet aggregation. This aggregation can be assessed by measuring the change in optical density (OD) of the PRP. The following in vitro test was used to evaluate the test compound for interference with the ADP-induced aggregation of guinea pigs.

Materials

Platelet rich plasma (PRP): Free-flowing blood is taken from a healthy volunteer or a guinea pig and collected in 0.1 volume sodium citrate.$2H_2O$, 3.8% in distilled $H_2O$ (w/v). The final concentration is 0.38% sodium citrate. The citrated blood is centrifuged at 1,600 N/kg (160 g, i.e., 900 rpm in a Hettich Rotanta/AP at room temperature. After 15 minutes centrifugation is discontinued with brake turned off, and the supernatant (=PRP) is collected. A fresh solution of ADP (analytical grade), 50 µM in 0.9% NaCl in MQ water, is used immediately.

In this assay, tirofiban (AGGRASTAT® (MSD) purchased as 0.25 mg/mL concentrate for i.v. infusion) inhibits human platelet aggregation induced by 5 µM ADP by 50% at a concentration of 30-60 nM (IC50).

Equipment

1. Sysmex blood cell counter model KX-21.
2. Labsystems iEMS reader MF with a 620 nm filter, an orbital shaker set at 1000 rpm and a constant temperature of 37° C. Absorption is measured with the Labsystems iEMS program.
3. Blood collection system 600 mL with needle, art P4203 (NPBI).
4. 96 wells flat bottom microplates (Greiner Labortechnik).

Procedure

The platelets in the supernatant (PRP) are counted using a Sysmex blood cell counter and the supernatant is diluted with PPP (platelet poor plasma) to obtain a PRP containing approximately 400,000±50,000 plt/mL. PRP should stabilize at room temperature for at least 20 min but not longer than 3 h.

150 µL PRP is pipetted into a well of the microplate. 30 µL test compound in a range of concentrations (7 concentrations per compound) or vehicle is added and the microplate is placed in the Labsystems iEMS reader MF at 37° C. The optical density ($OD_{620}$) is then measured at 620 nm. After shaking for 2 minutes in the reader (1,000 rpm), the OD is measured for the second time. This is to verify the stability of the platelets (absence of spontaneous platelet aggregation). Then, 20 µL of 50 µM ADP solution is added and the OD is kinetically measured every minute for 14 minutes at 620. Between two measurements, the plate is shaking for 40 seconds at 1,000 rpm. Each test compound is investigated in at least 2 experiments using PRP from different volunteers.

Evaluation of Response

The mean OD at each compound concentration (including vehicle) is calculated at t=0 min and t=10 min. The percentage inhibition at each concentration is calculated using the formula:

$$100\% - \frac{(ODcompound \text{ at } t = 0 \text{ min} - ODcompound \text{ at } t = 10 \text{ min})}{(ODvehicle \text{ at } t = 0 \text{ min} - ODvehicle \text{ at } t = 10 \text{ min})} \times 100\%$$

The IC50 of the test compound is the concentration at which the ADP-induced platelet aggregation is reduced by 50%. For this, the percentage inhibition values are plotted against compound concentration and the IC50 is calculated using Graphpad Prism 3.0 (with variable slope).

1.2 In Vitro Test for Inhibition of Human Platelet Aggregation Induced by TRAP

Addition of trombin receptor agonist peptide (TRAP) to washed human or guinea pig platelets (WPL) in vitro induces platelet aggregation. This aggregation can be determined by measuring the optical density of the WPL. The in vitro test described here is used to analyze the activity of a test compound to inhibit TRAP-induced aggregation of human platelets. A microplate reader is used to measure the activity of several compounds simultaneously.

Materials

*Composition of Watson Buffer:

| NaCl | 7.83 g (134 mmol) |
| KCl | 0.22 g (2.9 mmol) |
| $NaHCO_3$ | 1.01 g (12 mmol) |
| $Na_2HPO_4 \cdot 2H_2O$ | 0.06 g (0.34 mmol) |
| $MgCl_2 \cdot 6H_2O$ | 0.20 g (1 mmol) |
| Glucose | 0.90 g (5 mmol) |
| HEPES | 1.19 g (5 mmol) |
| $H_2O$ to | 1 L |

The pH is adjusted to 7.4 with NaOH (1 mol/L) TNP buffer.

*Composition of TNP-Buffer:

| Tromethamine (Tris) | 6.057 g (50 mmol) |
| NaCl | 5.844 g (100 mmol) |
| PEG6000 | 3.0 g |
| $H_2O$ to | 1 L |

The pH of the solution is adjusted to 7.4 at 37° C. with HCl (10 mol/L).

*$PGI_2$ Solution:

Prostaglandin $I_2$ stock solution of 1 mg/mL in KOH (1 mol/L) is stored at −20° C. Immediately before use a solution of 5 µg/mL in ice-cold NaCl (9.0 g/L) is prepared.

*Platelet Rich Plasma (PRP):

Free-flowing blood is taken from a healthy volunteer or a guinea pig and collected in 0.1 volume 3.8% sodium citrate.2H2O in MQ water (w/v). The final conncentration is 0.38% sodium citrate. The citrated blood is centrifuged at 1,600 N/kg (160 g) in Hettich Rotanta/AP centrifuge at room temperature. After 15 minutes, centrifugation is discontinued with the brake turned off. And the supernatant (=PRP) is collected and diluted with platelet poor plasma to obtain a suspension containing approximately 400 000 platelets/mL.

*Platelet Poor Plasma (PPP):

Citrated blood is centrifuged at approximately 20000 N/kg for 10 minutes at RT and the PPP is siphoned off.

*Washed Platelets (WPL):

An aliquot of 1 µL $PGI_2$ solution is added to 1 mL PRP and thereafter centrifuged at 20000 N/kg for 10 minutes at RT. The plasma is siphoned off and Watson buffer containing 5 ng/mL $PGI_2$ is added to the platelet pellet and the platelets are resuspended in the original volume by gently stirring with a plastic rod. The platelet suspension is centrifuged again at 20000 N/kg. The platelets are resuspended in Watson buffer in order to obtain a suspension containing approximately 400 000 platelets/mL.

*TRAP Solution:

TRAP is dissolved in $H_2O$ to give a solution containing 50 µmol/L. A fresh solution has to be prepared daily. For all aqueous solutions ultrapure $H_2O$ (Milli-Q quality) is used.

*Human Fibrinogen (Kordia/ERL, art nr: FIB 2 powder):

0.5 g fibrinogen powder is dissolved in 50 mL MQ water under vacuum. This stock solution is stored in aliquots of 100 µL at −20° C. Immediately before use, a solution of 0.5 mg/mL in saline is prepared.

In this assay, tirofiban (AGGRASTAT® (MSD)) purchased as 0.25 mg/mL concentrate for i.v. infusion) inhibits the human platelet aggregation induced by 5 µM TRAP by 50% at a final concentration of 30-60 nM (IC50).

Procedure

The WPL concentration is counted in a Sysmex blood cell counter and the suspension is diluted with Watson buffer to obtain a concentration of approximately 400,000 plt/mL. Before use WPL is allowed to stabilize at room temperature for at least 20 min but not longer than 3-4 hours.

150 µL WPL is pipetted into a well of a microplate. 15 µL of test compound solution or vehicle and 15 µL fibrinogen solution is added and the microplate is placed in the microplate reader at 37° C. Then, the opticaL density (OD) is measured at 405 nm and after shaking for 2 minutes in the reader, the $OD_{405}$ is measured again to verify the stability of the platelets (absence of spontaneous platelet aggregation). 20 µL of 50 µM TRAP solution is added and the $OD_{405}$ is kinetically measured every min for 14 min at 405 nm. Between two measurements, the plate is shaking for 40 seconds at 1,000 rpm. For determination of the $IC_{50}$ of a test compound, each compound is investigated in at least 2 experiments using WPL from different volunteers.

Evaluation of Responses:

The mean OD of each concentration (including vehicle) is calculated at t=0 min and t=10 min. The percentage inhibition at each concentration is calculated using Microsoft Excel with the formula:

$$100\% - \frac{(ODcompound \text{ at } t = 0 \text{ min} - ODcompound \text{ at } t = 10 \text{ min})}{(ODvehicle \text{ at } t = 0 \text{ min} - ODvehicle \text{ at } t = 10 \text{ min})} \times 100\%$$

The concentrations of the compound are plotted against the percentage inhibition. The $IC_{50}$ is calculated using Graphpad Prism 3.0 (with variable slope). The $IC_{50}$ of the test compound is the concentration at which the TRAP-induced platelet aggregation is reduced by 50%.

1.3 In Vitro Test for Determination of the Anti-Factor Xa Activity in Human Plasma The anti-factor Xa activity of the tested compounds in human plasma were measured amidolytically with S2222 (Chromogenix, Chromogenics Ltd, Molndal, Sweden) using the method described by Teien and Lie. (Teien A N, Lie M. Evaluation of an amidolytic heparin assay method increased sensitivity by adding purified antithrombin III. Thromb. Res. 1977, 10: 399-410). The anti-Xa activity is expressed in U/µmol after comparison of the amidolytic activity with a calibration curve of standard heparin.

TABLE 1

Summary of in vitro antithrombotic activities

| Compound | Anti-Xa U/μmol Human plasma pH 7.4 | Inhibition of human platelet aggregation (ADP) IC50 (nm) | Inhibition of human platelet aggregation (TRAP) IC50 (nm) | Inhibition of guinea pig platelet aggregation (ADP) IC50 (nm) |
|---|---|---|---|---|
| 28 | — | 43 | 41 | 493 |
| 27 | 1268 | — | — | — |
| 12 | 1392 | 92 | 65 | 127 |
| 10 | 927 | 74 | 72 | 225 |
| 17 | 1411 | 49 | 74 | 66 |

2.1 In Vitro Neutralization of the Antithrombotic Activity
A. In Vitro Neutralisation of Inhibition of Platelet Aggregation
(Pre-Incubation of Compound with Avidin)

As performed in above described protocol for ADP-induced platelet aggregation. The aggregation was performed in the presence of 225 nM compound 12 or 450 nM compound 10, concentrations at which maximal inhibition of the guinea pig platelet aggregation is achieved. Before inducing the guinea pig platelet aggregation by adding ADP, compound and avidin (from egg white, Sigma) in different concentrations were pre-incubated for 2 minutes at room temperature (FIGS. 1 and 2).

B. In Vitro Neutralisation of Inhibition of Platelet Aggregation
(After Delayed Addition of Avidin)

As performed in above described protocol for ADP-induced platelet aggregation. The aggregation was performed in the presence of 225 nM compound 12 or 450 nM compound 10, concentrations at which maximal inhibition of guinea pig or human platelet aggregation is achieved. After 7 minutes the detection of platelet aggregation was interrupted and avidin (from egg white, Sigma) in different concentrations was added at t=9 min. Within 1 minute the detection of the platelet aggregation was resumed (FIGS. 3 and 4).

In FIG. 5, the effect of avidin on the inhibition of human platelet aggregation by compound 17 is shown (addition of avidin 9 minutes after ADP-induced platelet aggregation).

Conclusion: administration of avidin to a guinea pig platelet aggregation assay containing compound 10 results in immediate restoration of platelet aggregation (=neutralisation of the antithrombotic, anti-GPIIbIIIa activity), whereas the inhibitory activity of the non-biotinylated equivalent antithrombotic compound 12 cannot be restored. Administration of avidin to compound 17 leads to full restoration of human platelet aggregation.

3.1 Pharmacokinetics

The pharmacokinetic properties of compounds 10, 12, 17 and 27 were studied in male Wistar rats of 300-400 gr. The rats were anaesthetized by inhalation of a mixture of $O_2N_2O$/isoflurane, after which the right jugular vein was cannulated. The next day rats were treated s.c. with doses of 100 or 500 nmol/kg. After s.c. administration, blood was sampled at several time intervals. Then the blood was centrifuged after which the plasma was siphoned off and stored at −20° C. until use. The concentration of the tested compound was measured amidolytically with S2222 (Chromogenix, Chromogenics Ltd, Molndal, Sweden) by determination of the anti-Xa activity based on the method of Teien and Lie in the obtained plasma samples against a calibration curve which was made of the stock solution of the tested compound itself. (Teien A N, Lie M. Evaluation of an amidolytic heparin assay method increased sensitivity by adding purified antithrombin III. Thromb. Res. 1977, 10: 399-410). The concentration in the samples was expressed in nmol/mL and the kinetic parameters were calculated with the noncompartment model of WinNonlin. (FIGS. 6 and 7)

TABLE 2

Pharmacokinetic parameters after s.c. administration of compound 10 or 12 (500 nmol/kg) in rat.

| | Compound 10 Mean ± s.e.m. | Compound 12 Mean ± s.e.m. |
|---|---|---|
| Tmax (h) | 1.3 | 2.5 |
| Cmax (nmol/mL) | 4.5 ± 0.4 | 5.0 ± 0.4 |
| T½ eli (h) | 10.7 ± 1.5 | 9.3 ± 0.2 |
| AUCinf (h · nmol/mL) | 76.2 ± 2.8 | 75.3 ± 3.2 |
| Vz (mL/kg) | 103 ± 9 | 90 ± 5 |
| Cl (mL/h/kg) | 6.6 ± 0.3 | 6.7 ± 0.3 |

Experiment performed in n = 3/treatment.

TABLE 3

Pharmacokinetic parameters after s.c. administration of compound 12, 17, or 27 (100 nmol/kg) in rat.

| | Compound 12 (dual inhibitor reference) Mean ± s.e.m. | Compound 17 Mean ± s.e.m. | Compound 27 (pentasaccharide reference) Mean ± s.e.m. |
|---|---|---|---|
| Tmax (h) | 1.3 | 1.7 | 0.9 |
| Cmax (nmol/mL) | 1.26 ± 0.02 | 1.24 ± 0.01 | 0.92 ± 0.05 |
| T½ eli (h) | 9.8 ± 0.4 | 10.4 ± 0.5 | 12.6 ± 0.8 |
| AUCinf (h · nmol/mL) | 16.8 ± 0.5 | 15.9 ± 0.9 | 11.5 ± 0.6 |
| Vz (mL/kg) | 84 ± 2 | 95 ± 6 | 159 ± 11 |
| Cl (mL/h/kg) | 6.0 ± 0.2 | 6.3 ± 0.3 | 8.8 ± 0.5 |

Experiment performed in n = 3/treatment.

It is concluded that within the variability of the experiment compounds 10, 12, 17 and 27 show the same pharmacokinetic behavior in rats.

3.2 Pharmacokinetics—Neutralization Experiment:

Rats were treated with compound 10, 12, or 27 at a dose of 100 nmol/kg s.c. At t=1 h, a blood sample was taken and 10 mg/kg of Avidin (from egg white, Sigma) was administered i.v. to the rats treated with compound 10 or 12. Blood was sampled at 0.5-1-3-6 and 23 hours subsequently. The blood was treated as described in the pharmacokinetic experiment and the concentration of the samples was determined by measuring the (residual) anti-Xa activity. (FIG. 8)

TABLE 4

Pharmacokinetic parameters after s.c. administration of 100 nmol/kg of compound 10 or 12 and avidin (10 mg/kg) at t = 1 h.

|  | Compound 10 (+avidin at t = 1 h) Mean ± s.e.m. | Compound 12 (+avidin at t = 1 h) (dual inhibitor reference) Mean ± s.e.m. |
| --- | --- | --- |
| Tmax (h) | 1.0 | 1.3 |
| Cmax (nmol/mL) | 1.03 ± 0.1 | 1.21 ± 0.08 |
| T½ eli (h) | 0.9 ± 0.05 | 11.7 ± 1.1 |
| AUCinf (h · nmol/mL) | 1.6 ± 0.2 | 15.7 ± 0.4 |
| Vz (mL/kg) | 82 ± 6 | 107 ± 7 |
| Cl (mL/h/kg) | 61.7 ± 5.6 | 6.4 ± 0.2 |

Experiment performed in n = 3/treatment.

It is concluded that after s.c. administration of compound 10 (100 nmol/kg), the antithrombotic activity as determined by measuring the (residual) anti-Xa activity can be neutralized by administration of 10 mg/kg i.v. of avidin. The neutralization of compound 10 by avidin is reflected by the strongly reduced overall T1/2 eli, the strongly reduced overall AUCinf and the strongly increased Cl in comparison to compound 12. Furthermore, the pharmacokinetic behavior of the non-biotinylated equivalent compound 12 is not affected by the addition of avidin (also when compared to the reference pentasaccharide 27 which shows a similar profile). The latter confirms that the neutralization is associated with the presence of the biotin label and that it does not affect the pharmacokinetic behavior of the dual inhibitor.

In a separate experiment compound 10, 17 or 26 was administered at a dose of 500 nmol/kg s.c. after which blood was collected at 24 hours. Then 10 mg/kg avidin was administered intravenously and blood was collected at 25 and 26 hours. (FIG. 9)

TABLE 5

Plasma levels after s.c. administration of 500 nmol/kg of compound 10, 17 and 26 at 24 hours and 2 hours after avidin (10 mg/kg i.v.) administration at t = 24 h.

|  | Compound 10 (nmol/mL) | Compound 17 (nmol/mL) | Compound 26 (nmol/mL) |
| --- | --- | --- | --- |
| T = 24 h | 0.733 ± 0.033 | 0.666 ± 0.093 | 1.071 ± 0.058 |
| avidin at T = 24u05 in all cases | | | |
| T = 26 h | 0.185 ± 0.045 | 0.112 ± 0.035 | 0.361 ± 0.026 |
| % reduction | 75% | 83% | 66% |

Experiment performed in n = 3/treatment, values are given in mean ± sem.

It is concluded that within 2 hours after administration of avidin (10 mg/kg) the plasma concentration of compounds 10, 17 and 26 was reduced by with 75, 83 and 66%, respectively. The experiment was performed 24 h after s.c. administration of the biotinylated compounds, which reveals that the linker between biotin moiety and the antitbrombotic compound is stable in vivo.

4. In Vivo Neutralization of the Antithrombotic Activity

An intravascular infusion of a collagen suspension induces platelet aggregation and causes transient thrombocytopenia in rats. This test is used to evaluate the influence of a test compound on the severity of thrombocytopenia induced by collagen in rats.

In the first experiment male guinea pigs were s.c. treated with compound 10 at a dose of 75 nmol/kg or vehicle at 4 hours before collagen infusion. In a second experiment compounds 12 and 17 were s.c. administered at a dose of 100 nmol/kg at the same time-point. Male guinea pigs were anaesthetized by i.m. administration of Ketamine+Sedamun (90+ 10 mg/kg, respectively). After 15 minutes one of the common carotid arteries was dissected free and cannulated with a PE 50 cannula (Clay Adams). Two blood samples of 0.5 mL were collected in plastic vials containing 25 µL 0.20 M Na$_2$EDTA solution. The cannula was then connected to a syringe containing 0.25 mg/mL collagen suspension (Hormon Chemie, Munich, West Germany, diluted with isotonic buffer of pH 2.8). This suspension was administered via an infusion of 225 µL during 30 seconds. Then the syringe was disconnected and 2 blood samples of 0.5 mL were taken at 85 and 95 seconds after the start of the collagen infusion. Then the animals were killed with euthasate after which the number of platelets per sample were counted with a Sysmex blood cell counter model KX-21. In case avidin was used, 10 mg/kg of avidin was i.v. administered at t=4 h after s.c. administration of compound 10, 12 or 17 after which collagen was infused within 5 minutes.

After counting the number of platelets in the collected blood samples the decreased number of platelets is calculated by dividing the mean platelet number of the blood samples obtained at t=85 and 95 seconds by the mean value of the blood samples obtained at t=0. The test was carried out with n=4.

TABLE 6

Platelet counts after administration of compound 10 (75 nmol/kg) with or without avidin in an in vivo (guinea pig) model based on collagen induced platelet aggregation

| Treatment (75 nmol/kg) | No. of platelets t = 0 | No. of platelets t = 90 sec | % remaining platelets | % inhibition |
|---|---|---|---|---|
| Control group | 390 ± 23 | 158 ± 42 | 39.2 ± 7.6 | 0 |
| Compound 10 | 386 ± 31 | 328 ± 18 | 85.3 ± 2.5 | 76 ± 4 |
| Compound 10 + avidin | 384 ± 20 | 152 ± 26 | 40.4 ± 7.8 | 2 ± 13 |

TABLE 7

Platelet counts after administration of compound 12 or 17 (100 nmol/kg s.c.) with or without avidin in an in vivo (guinea pig) model based on collagen induced platelet aggregation

| Treatment (100 nmol/kg) | No. of platelets t = 0 | No. of platelets t = 90 sec | % remaining platelets | % inhibition |
|---|---|---|---|---|
| Control group | 391 ± 12 | 192 ± 13 | 49.0 ± 3.9 | 0 |
| Compound 12 | 426 ± 6 | 360 ± 7 | 84.5 ± 2.2 | 70 ± 4 |
| Compound 12 + avidin | 379 ± 6 | 329 ± 11 | 86.5 ± 1.7 | 74 ± 3 |
| Compound 17 | 424 ± 11 | 348 ± 7 | 82.5 ± 2.0 | 66 ± 4 |
| Compound 17 + avidin | 367 ± 16 | 181 ± 12 | 46.5 ± 7.8 | −5 ± 15 |

After a dose of 75 nmol/kg s.c. of compound 10 or 100 nmol/kg s.c. of compound 12 or 17, compounds inhibited collagen induced platelet aggregation by more than 66% at 4 hours after administration. Administration of 10 mg/kg avidin just prior to collagen infusion caused an immediate and quantitative neutralization of the platelet inhibitory activity of compounds 10 and 17, but not of compound 12, the compound lacking the biotin moiety. These results show that neutralization of anti-GPIIbIIIa mediated antiplatelet activities of compounds 10 and 17 is solely mediated by the biotin label and is based on a specific binding to avidin. Moreover, comparison of the relative reduction in platelet counts effected by compounds 10, 12 and 17 reveals that the biotin label does not interfere with the intrinsic antiplatelet activity of the dual inhibitors.

Further Pharmacology

A dose-dependent bleeding, induced in guinea pigs after administration of compound 17, was stopped immediately by administration of avidin (i.v. 10 mg/kg).

What is claimed is:

1. An antithrombotic compound of the formula I oligosaccharide-spacer-GpIIb/IIIa antagonist (I), wherein the oligosaccharide is a negatively charged pentasaccharide residue of Formula B

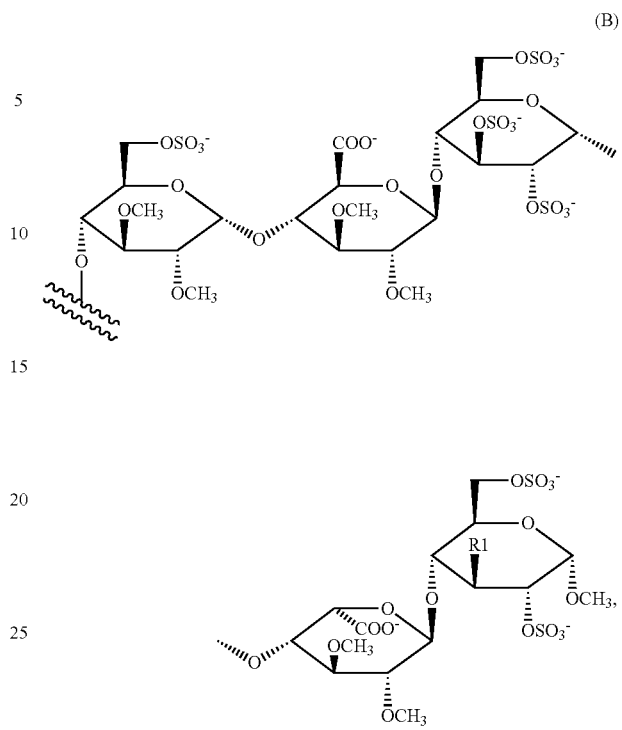

wherein R1 is $OCH_3$ or $OSO_3^-$, the charge being compensated by positively charged counterions;

the spacer is an essentially pharmacologically inactive linking residue;

the GpIIb/IIIa antagonist is a residue derived from tirofiban (MK 383);

or a pharmaceutically acceptable salt thereof;

wherein the spacer of the compound of formula I comprises a covalent bond with a biotin label.

2. The compound of any one of claim 1, wherein the spacer of the compound of formula I comprises one covalent bond with a biotin analogue of the formula —$(CH_2)_4$—X-BT, wherein X=NH, N(1-4C)alkyl, NH—CH($CH_2$OH)—$CH_2$—C(O)—NH, NH—CH($CH_3$)—$CH_2$—C(O)—NH, NH—CH(COOH)—$CH_2$—C(O)—NH or NH—CH($CH_2$COOH)—$CH_2$—C(O)—NH, and wherein BT is the label

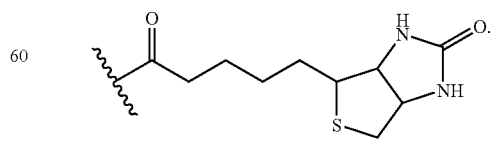

3. The compound of claim 2, being
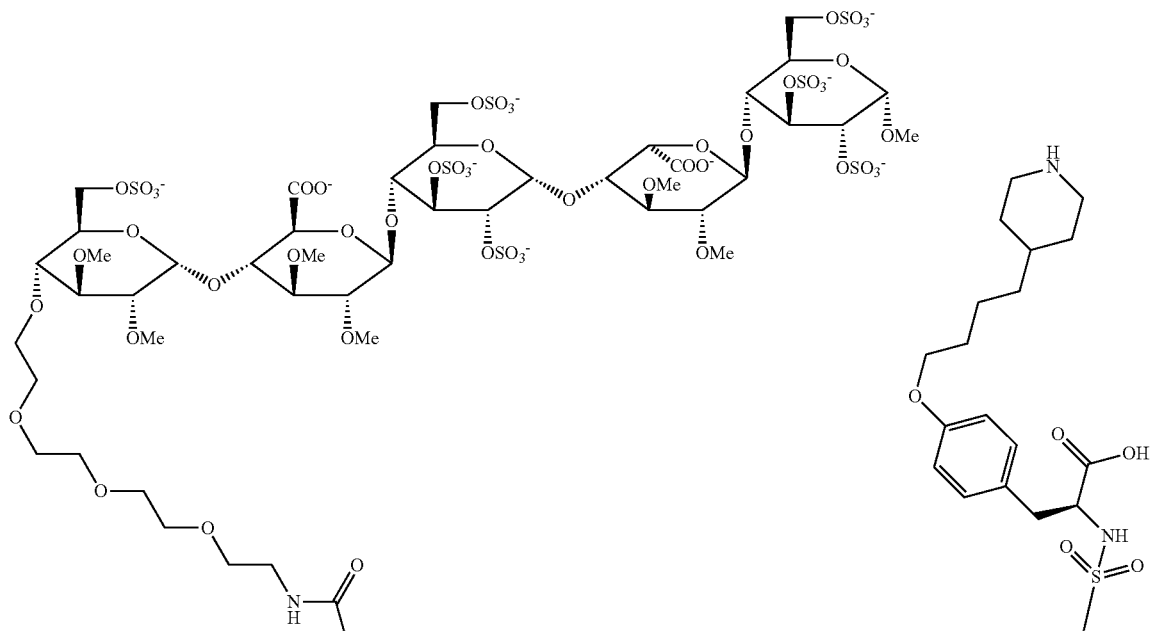
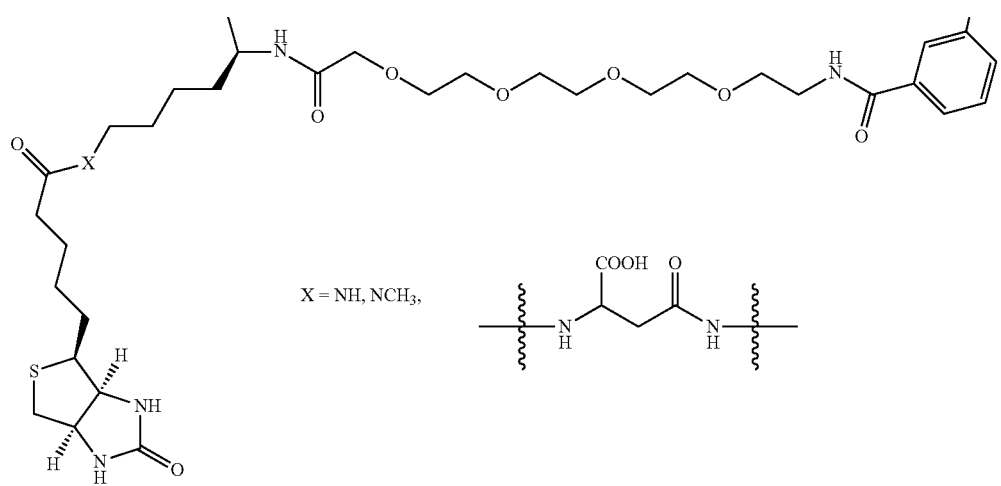

4. The compound of claim 3, being in the form of its sodium salt.

5. The compound of claim 4, being

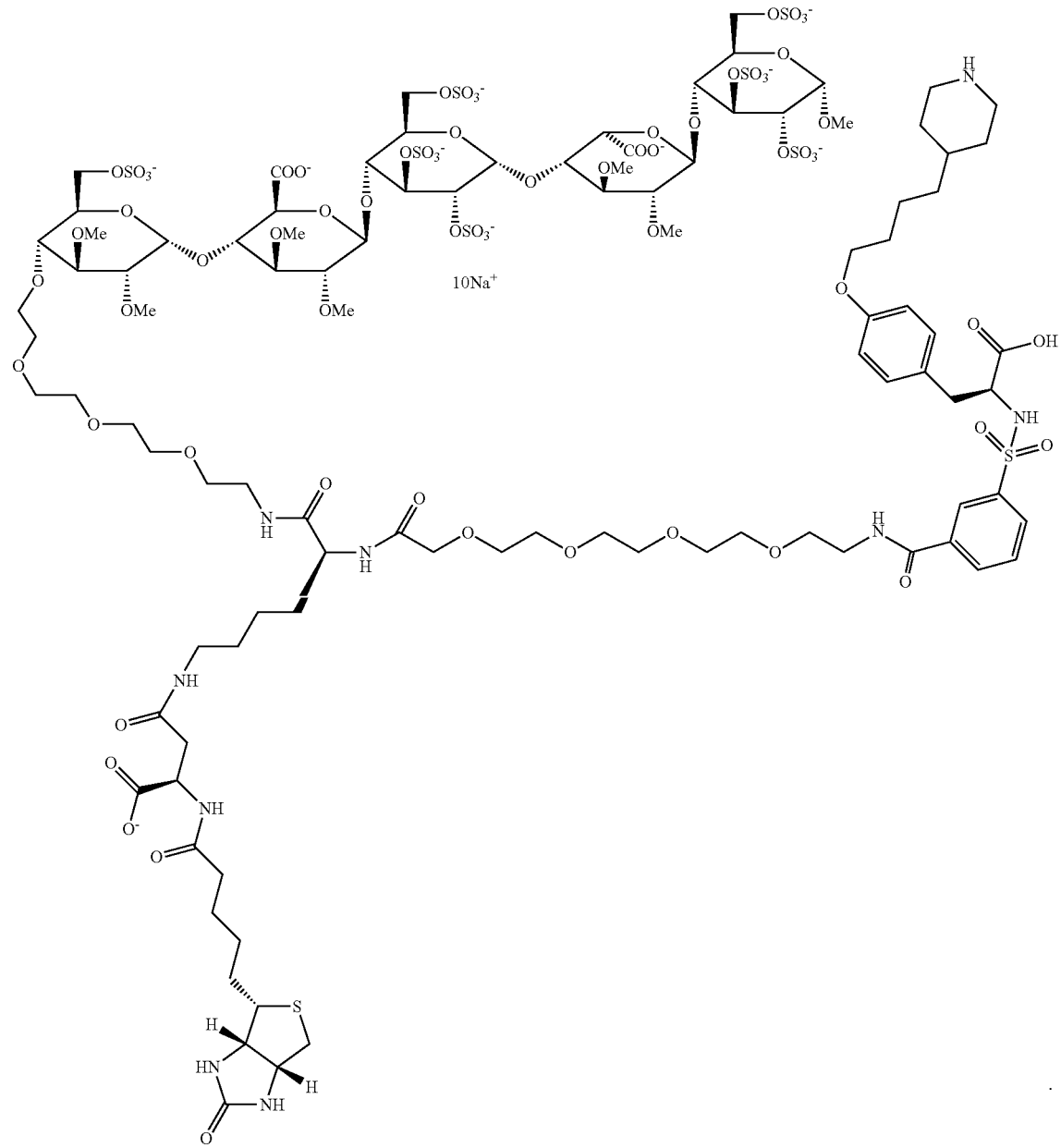

6. A pharmaceutical composition comprising the compound of any one of claim 1 and claims 2-5 and pharmaceutically suitable auxiliaries.

7. A method for treating thrombosis in a patient, the method comprising administering to the patient an effective amount of the compound according to claim 1.

* * * * *